US 10,094,769 B2

United States Patent
Hirata et al.

(10) Patent No.: US 10,094,769 B2
(45) Date of Patent: Oct. 9, 2018

(54) SUBSTANCE DETECTION SENSOR, SUBSTANCE DETECTING METHOD, AND SUBSTANCE DETECTION SYSTEM HAVING DUAL LIGHT SOURCE WITH OPTICAL SCANNING

(71) Applicant: PANASONIC INTELLECTUAL PROPERTY MANAGEMENT CO., LTD., Osaka (JP)

(72) Inventors: Keiji Hirata, Fukuoka (JP); Yuuji Terashima, Fukuoka (JP); Kazuhiro Yanagi, Fukuoka (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 100 days.

(21) Appl. No.: 15/506,065

(22) PCT Filed: Jul. 22, 2015

(86) PCT No.: PCT/JP2015/003666
§ 371 (c)(1),
(2) Date: Feb. 23, 2017

(87) PCT Pub. No.: WO2016/031128
PCT Pub. Date: Mar. 3, 2016

(65) Prior Publication Data
US 2017/0261426 A1 Sep. 14, 2017

(30) Foreign Application Priority Data
Aug. 27, 2014 (JP) .................................. 2014-173106

(51) Int. Cl.
G01N 21/31 (2006.01)
G01N 21/27 (2006.01)
(Continued)

(52) U.S. Cl.
CPC ....... *G01N 21/3151* (2013.01); *G01N 21/256* (2013.01); *G01N 21/27* (2013.01);
(Continued)

(58) Field of Classification Search
CPC .... G01N 21/3151; G01N 21/27; G01N 21/35; G01N 21/3554; G01V 8/10
(Continued)

(56) References Cited

U.S. PATENT DOCUMENTS 6,977,724 B2 * 12/2005 Knebel ................. G01J 3/1256
250/458.1

FOREIGN PATENT DOCUMENTS

JP 04-328449 11/1992
JP 07-243958 9/1995
(Continued)

OTHER PUBLICATIONS

International Search Report, dated Oct. 20, 2015 by the Japan Patent Office (JPO), in corresponding International Application No. PCT/JP2015/003666.

*Primary Examiner* — Que T Le
(74) *Attorney, Agent, or Firm* — Greenblum & Bernstein, P.L.C.

(57) ABSTRACT

A substance detection sensor includes a first light source, a second light source, and a substance detector. The first light source irradiates a detection area including a plurality of target areas with reference light having a first wavelength through surface irradiation using optical scanning. The second light source irradiates the detection area with first measuring light having a second wavelength different from the first wavelength through the surface irradiation using the optical scanning. The substance detector detects a specific substance in the detection area based on reflection light of the reference light from the first light source and reflection
(Continued)

light of the first measuring light from the second light source.

19 Claims, 26 Drawing Sheets

(51) Int. Cl.
*G01V 8/10* (2006.01)
*G01N 21/35* (2014.01)
*G01S 17/10* (2006.01)
*G01S 17/42* (2006.01)
*G01S 17/88* (2006.01)
*G01N 21/25* (2006.01)
*G01N 21/47* (2006.01)
*G01N 21/17* (2006.01)

(52) U.S. Cl.
CPC ............. *G01N 21/35* (2013.01); *G01N 21/47* (2013.01); *G01S 17/10* (2013.01); *G01S 17/42* (2013.01); *G01S 17/88* (2013.01); *G01V 8/10* (2013.01); *B60T 2210/10* (2013.01); *G01N 2021/1793* (2013.01); *G01N 2021/3155* (2013.01); *G01N 2201/101* (2013.01)

(58) Field of Classification Search
USPC .................................................. 250/221, 216
See application file for complete search history.

(56) References Cited

FOREIGN PATENT DOCUMENTS

| | | |
|---|---|---|
| JP | 09-061351 | 3/1997 |
| JP | 2001-116690 A | 4/2001 |
| JP | 2007-316049 | 12/2007 |

* cited by examiner

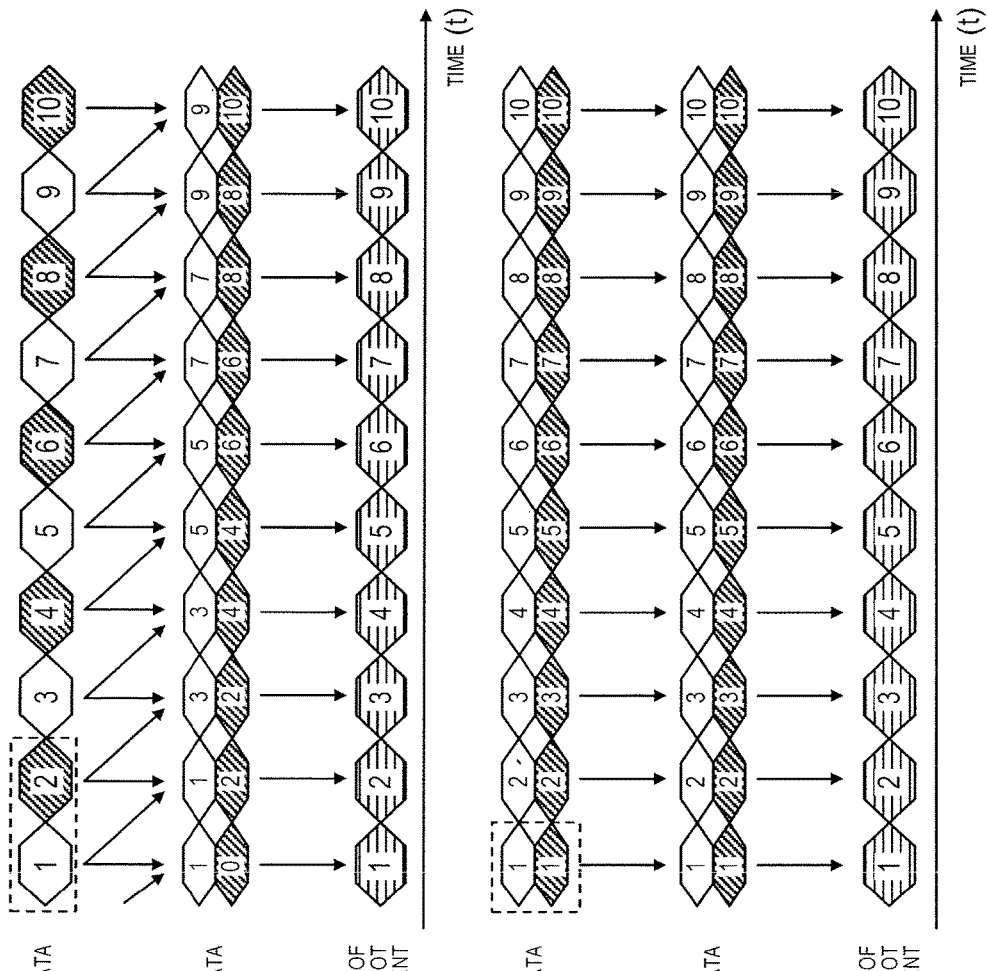

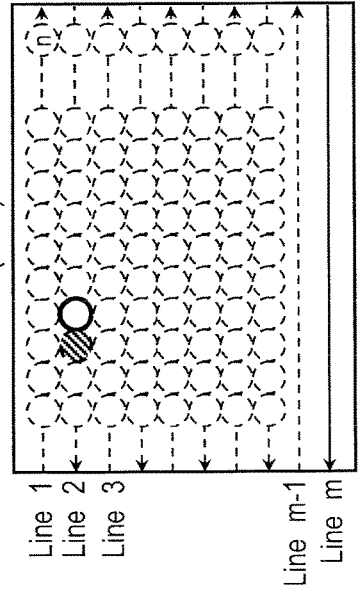
FIG. 16A t(n)
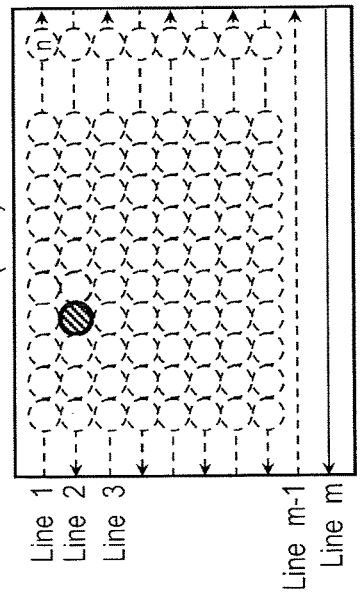
FIG. 16C t(n+2)
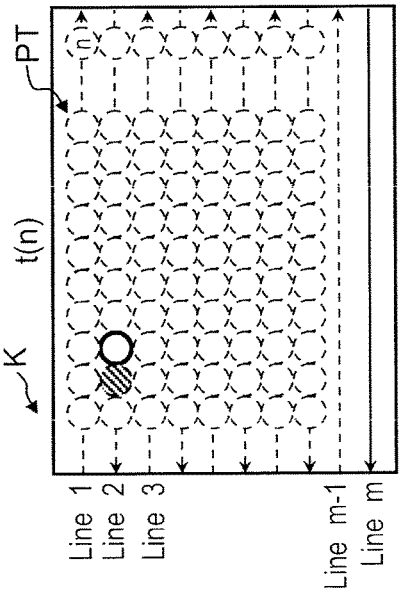
FIG. 16B t(n+1)
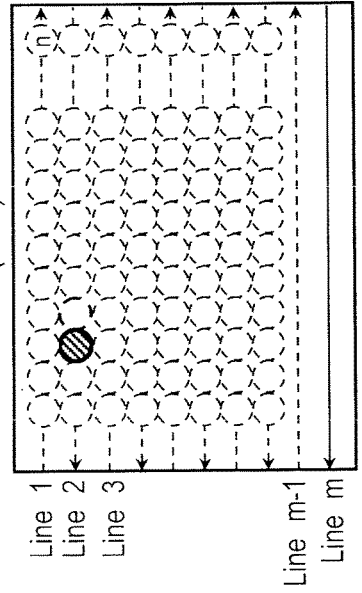
FIG. 16D t(n+3)

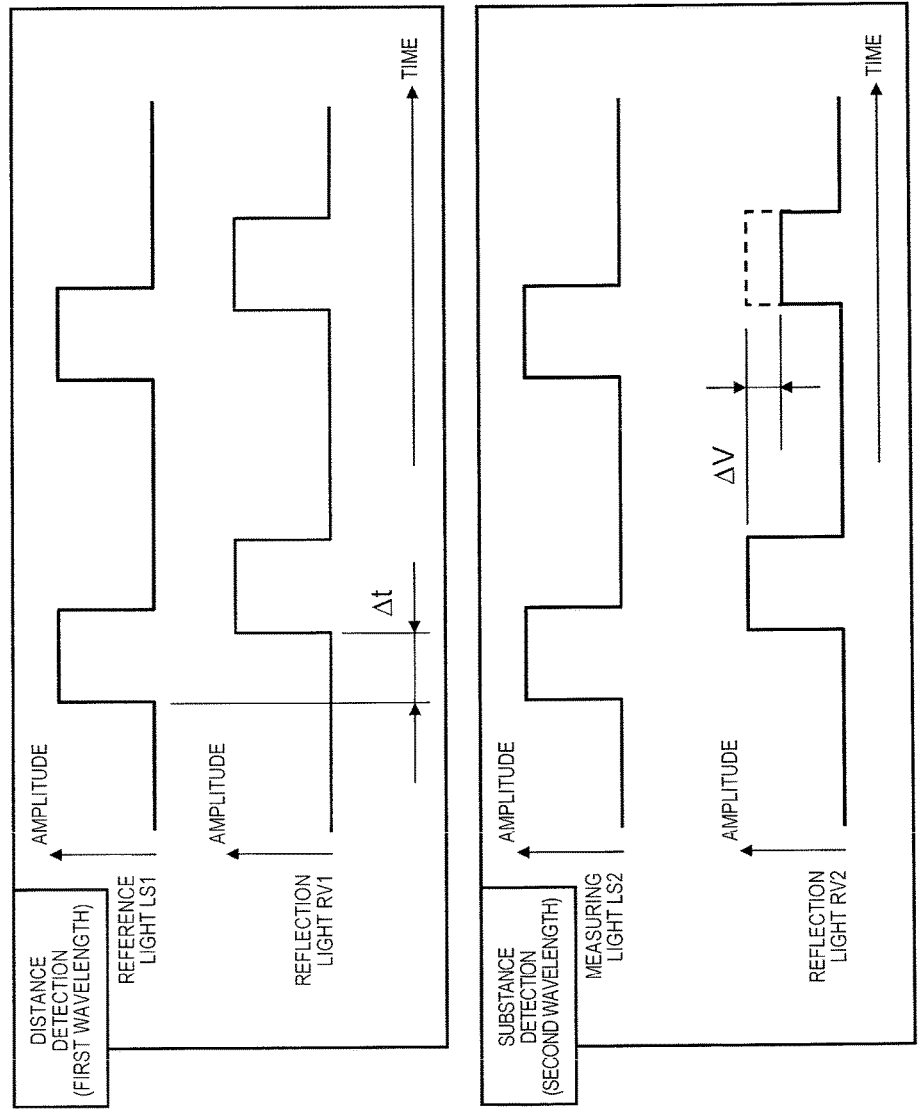

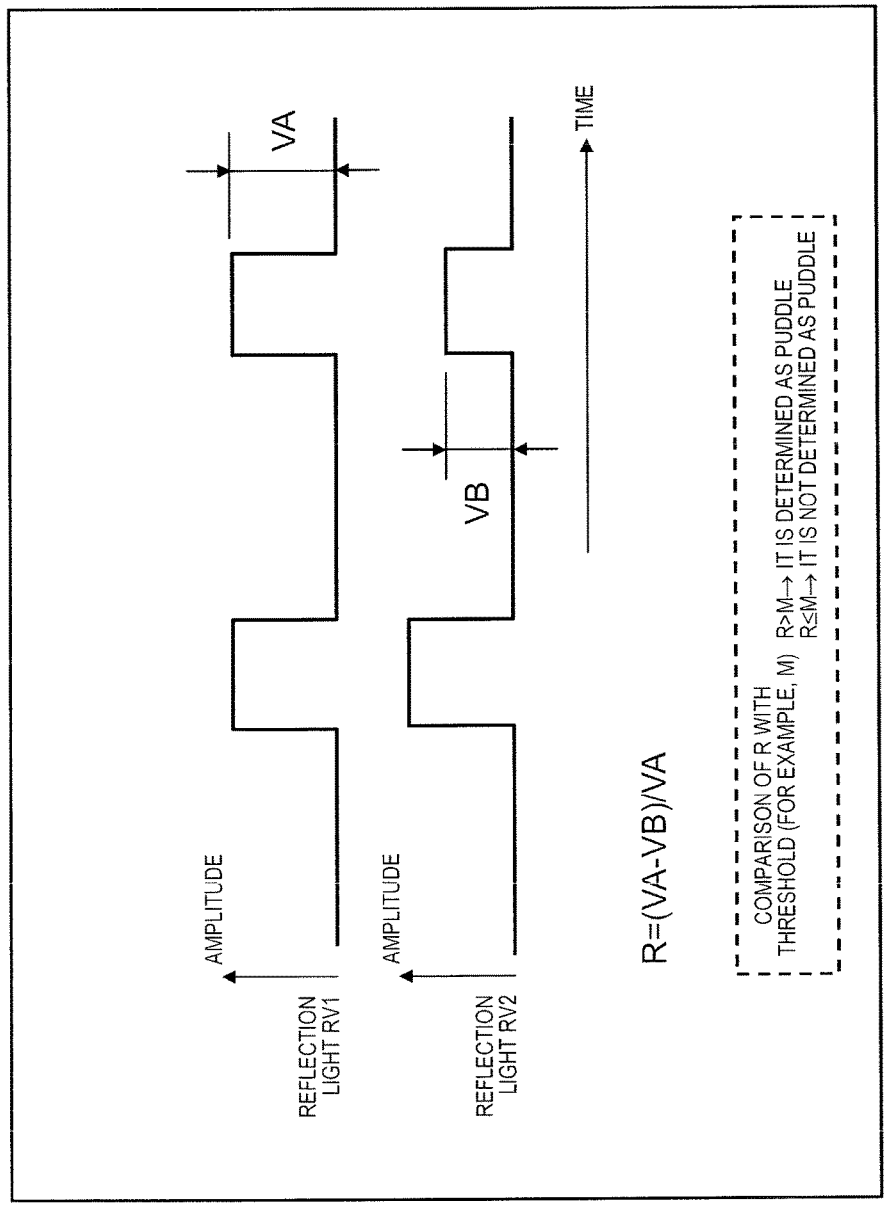

SUBSTANCE DETECTION SENSOR, SUBSTANCE DETECTING METHOD, AND SUBSTANCE DETECTION SYSTEM HAVING DUAL LIGHT SOURCE WITH OPTICAL SCANNING

TECHNICAL FIELD

The present disclosure relates to a substance detection sensor, a substance detection method, and a substance detection system that output image data related to a detection result of a measuring target substance.

BACKGROUND ART

As a method of detecting whether or not a measuring target substance (for example, water) is included in an object, a water measurement method of measuring water of the measuring target for each pixel based on two-dimensional image data of each pixel acquired by imaging the measuring target using measuring light which is within an absorption wavelength range of water and two-dimensional image data of each pixel acquired by imaging the measuring target using reference light which is not within the absorption wavelength range of water has been known (for example, see PTL 1).

A road surface monitoring system which includes a mechanism which swings an output direction of a laser beam up, down, left, and right and remotely monitors a road-surface state using the swing mechanism of the laser beam by performing surface irradiation on a road surface while varying an incidence angle in a range of α° in the up and down direction and in a range of β° in the left and right direction and receiving reflection light of the laser beam generated through the surface irradiation has been known (for example, see PTL 2).

CITATION LIST

Patent Literature

PTL 1: Japanese Patent Unexamined Publication No. 4-328449
PTL 2: Japanese Patent Unexamined Publication No. 2007-316049

SUMMARY OF THE INVENTION

The swing mechanism controls the output direction, and thus, the surface irradiation can be performed using the measuring light. Thus, it is possible to monitor whether or not the measuring target substance (for example, water) is present in a predetermined area (detection area). For example, the detection result of water which is the measuring target substance may be reflected on visible light image imaged by a camera.

However, in a case where the surface irradiation is performed on the detection area with the laser beam by using the mechanical swing mechanism, it may take time to perform the surface irradiation on the entire detection area. In a case where the surface irradiation is performed on the detection area with the measuring light and is subsequently performed on the detection area with the reference light, there may be a change between a status of the detection area during the surface irradiation using the measuring light and a status of the detection area during the surface irradiation using the reference light.

For example, a person does not exist in the detection area during the surface irradiation using the measuring light, but a person appears in the detection area during the surface irradiation using the reference light in some cases. A contrary phenomenon to the above-described phenomenon may be sufficiently observed to happen. In this case, even though information acquired by receiving the reflection light of the measuring light and information acquired by receiving the reflection light of the reference light are compared, since there is a temporal difference between these information items, it is difficult to accurately detect the measuring target substance, and erroneous detection of the measuring target substance is performed.

An object of the present disclosure is to a substance detection sensor, a substance detection method, and a substance detection system which reduce a time difference between projection timings of measuring light and reference light onto a predetermined detection area and suppress erroneous detection of a measuring target substance in the detection area.

A substance detection sensor according to the present disclosure includes a first light source, a second light source, and a substance detector. The first light source irradiates a detection area including a plurality of target areas with reference light having a first wavelength through surface irradiation using optical scanning. The second light source irradiates the detection area with first measuring light having a second wavelength different from the first wavelength through the surface irradiation using the optical scanning. The substance detector detects a specific substance in the detection area based on reflection light of the reference light from the first light source and reflection light of the first measuring light from the second light source.

In a substance detection method of the substance detection sensor according to the present disclosure, a detection area including a plurality of target areas is irradiated with reference light having a first wavelength from a first light source through surface irradiation using optical scanning. The detection area is irradiated with first measuring light having a second wavelength different from the first wavelength from a second light source through the surface irradiation using the optical scanning. A specific substance is detected in the detection area based on reflection light of the reference light from the first light source and reflection light of the first measuring light from the second light source.

In a substance detection system according to the present disclosure, a substance detection sensor and an external connection device are connected. The substance detection sensor includes a first light source, a second light source, a substance detector, and an output. The first light source irradiates a detection area including a plurality of target areas with reference light having a first wavelength through surface irradiation using optical scanning. The second light source irradiates the detection area with first measuring light having a second wavelength different from the first wavelength through the surface irradiation using the optical scanning. The substance detector detects a specific substance in the detection area based on reflection light of the reference light from the first light source and reflection light of the first measuring light from the second light source. The output outputs information related to the specific substance detected by the substance detector to the external connection device.

According to the present disclosure, it is possible to reduce a time difference between projection timings of measuring light and reference light onto a predetermined detection area, and it is possible to suppress erroneous detection of a measuring target substance in the detection area.

BRIEF DESCRIPTION OF DRAWINGS

FIG. 11A is an explanatory diagram showing an example of timings of projection of the first projection light source and the second projection light source and a detection process of the measuring target substance according to a comparative example.

FIG. 11B is an explanatory diagram showing an example of timings of projection of the first projection light source and the second projection light source and a detection process of a measuring target substance according to the first exemplary embodiment.

FIG. 16A is an explanatory diagram showing an example of images of projection positions of the first projection light source and the second projection lily source in the eighth projection pattern and the ninth projection pattern in a sequence of time.

FIG. 16B is an explanatory diagram showing an example of the images of the projection positions of the first projection light source and the second projection light source in the eighth projection pattern and the ninth projection pattern in a sequence of time.

FIG. 16C is an explanatory diagram showing an example of the images of the projection positions of the first projection light source and the second projection light source in the eighth projection pattern and the ninth projection pattern in a sequence of time.

FIG. 16D is an explanatory diagram showing an example of the images of the projection positions of the first projection light source and the second projection light source in the eighth projection pattern and the ninth projection pattern in a sequence of time.

FIG. 20A is a principle explanatory diagram of distance detection using reference light having a first wavelength of different two kinds of wavelengths in the invisible light sensor according to the first exemplary embodiment.

FIG. 20B is a principle explanatory diagram of substance detection using reference light and measuring light having two different kinds of wavelengths in the invisible light sensor according to the first exemplary embodiment.

FIG. 21 is an outline explanatory diagram of the substance detection in the invisible light sensor according to the first exemplary embodiment.

DESCRIPTION OF EMBODIMENTS

Hereinafter, exemplary embodiments of a substance detection sensor, a substance detection method, and a substance detection system according to the present disclosure will be described with reference to the drawings. An invisible light sensor will be described as an example of a substance detection sensor according to the respective exemplary embodiments. The present disclosure may be described as a substance detection method including the respective operations (steps) performed by the invisible light sensor as the example of the substance detection sensor or a substance detection system including the invisible light sensor as the example of the substance detection sensor.

(Outline of Detection Camera Including Invisible Light Sensor)

Figure 1:
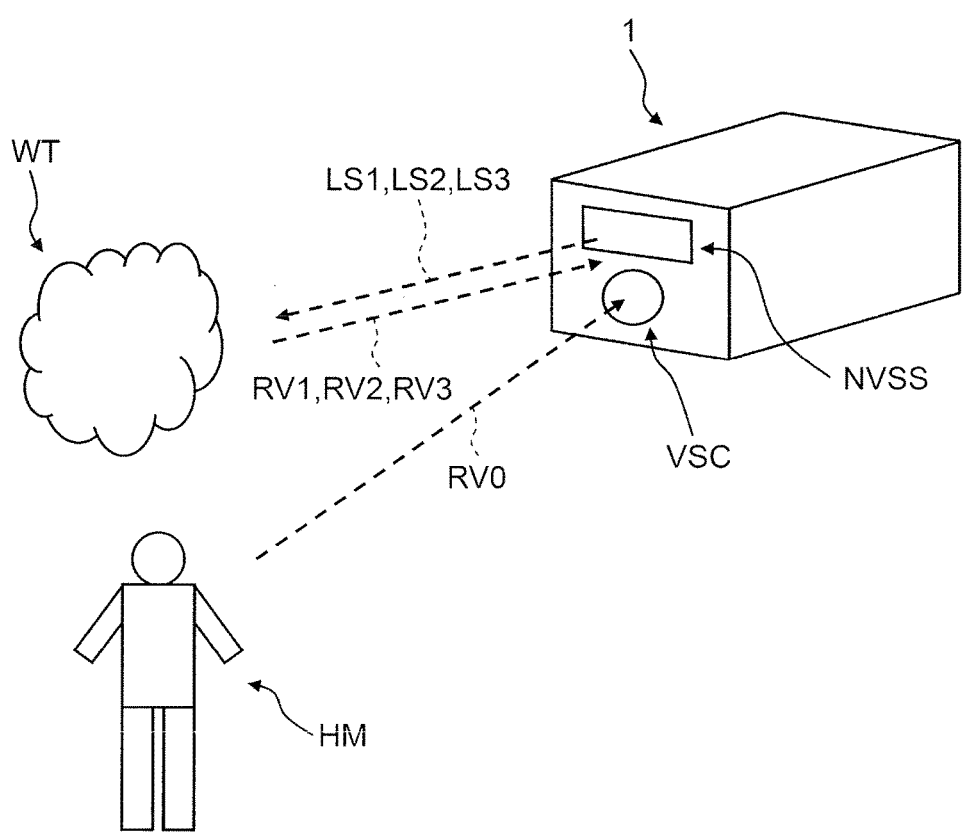
FIG. 1 is an outline explanatory diagram of a detection camera including an invisible light sensor according to the respective exemplary embodiments.

FIG. 1 is an outline explanatory diagram of detection camera 1 including invisible light sensor NVSS according to the respective exemplary embodiments. Detection camera 1 shown in FIG. 1 includes visible light camera VSC, invisible light sensor NVSS. For example, similarly to an existing monitoring camera, visible light camera VSC images person HM or an object (not shown) present in a predetermined detection area (detection area K) by using reflection light RV0 of visible light having a predetermined wavelength (for example, 0.4 to 0.7 µm). Hereinafter, output image data imaged by visible light camera VSC is referred to as "visible-light-camera image data". Accordingly, detection camera 1 is described as an example of an image output device that has both configurations of invisible light sensor NVSS as an example of the substance detection sensor according to the present disclosure and visible light camera VSC which acquires the visible-light-camera image data by imaging.

Invisible light sensor NVSS projects reference light LS1 and measuring light LS2 which are invisible light beams (for example, infrared light beams) having predetermined wavelengths different from each other (to be described below) on the same detection area K as that of visible light camera VSC through surface irradiation using optical scanning. Reference light LS1 is used for measuring a distance between a specific substance (for example, water such as puddle WT) which is a measuring target substance and invisible light sensor NVSS, is light having a wavelength which does not belong to an absorption wavelength range of the specific substance, and is used for providing reference data at the time of comparison in a process of detecting whether or not the specific substance is present. Meanwhile, measuring light LS2 is light having a wavelength which belongs to the absorption wavelength range of the specific substance, and is used for providing data indicating detection of the specific substance (target) at the time of comparison in the process of detecting whether or not the specific substance is present.

Invisible light sensor NVSS determines whether or not the specific substance is detected in detection area K by using reference reflection light RV1 and measuring reflection light RV2 acquired through reflection of reference light LS1 and measuring light LS2 from an object (for example, water such as puddle WT) to be detected. For example, the specific substance which is a determining target on which invisible light sensor NVSS performs the determination of whether or not the specific substance is present is a substance which is difficult to be discriminated using the visible-light-camera image data of visible light camera VSC at a glance. Hereinafter, "puddle WT" will be described as an example of the specific substance, but the specific substance is not limited to puddle WT. For example, the specific substance may be gas.

Detection camera 1 generates display data acquired by combining output image data (hereinafter, referred to as "substance position image data") equivalent to the determination result of whether or not the specific substance is detected in invisible light sensor NVSS or information, related to the substance position image data with the visible-light-camera image data imaged by visible light camera VSC, and outputs the generated display data. An output destination of the display data from detection camera 1 is an external connection device connected to detection camera 1 via a network (not shown), and is, for example, camera server CS or communication terminal MT shown in FIG. 3. The network may be a wired network (for example, intranet or Internet), and a wireless network (for example, wireless local area network (LAN)).

Figure 2:
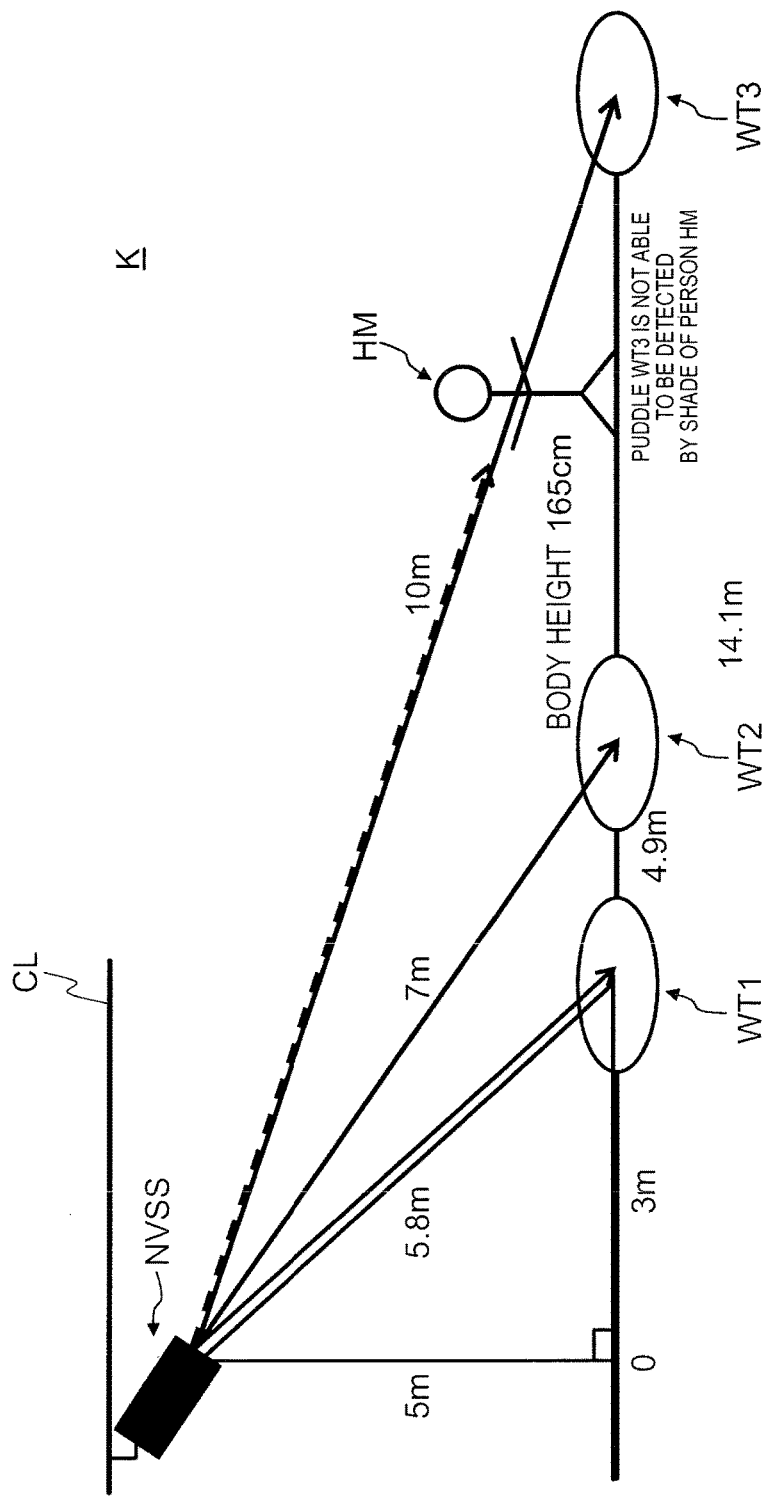
FIG. 2 is a schematic diagram showing an example of a utilization image of the invisible light sensor according to the respective exemplary embodiments.

FIG. 2 is a schematic diagram showing an example of a utilization image of invisible light sensor NVSS according to the respective exemplary embodiments. For example, invisible light sensor NVSS is attached to a ceiling surface, and detects puddle WT1 which is located so as to be 3 m distant from a floor surface (point O) located directly under so as to be 5 m distant from an installation position of invisible light sensor NVSS in detection area K and puddle WT2 which is located so as to be 4.9 m distant therefrom. Invisible light sensor NVSS detects that distances between puddle WT1 and puddle WT2 and the installation position of invisible light sensor NVSS are respectively 5.8 m and 7 m.

However, when invisible light sensor NVSS tries to detect puddle WT3 which is located so as to be 14.1 m distant from the floor surface (point O) located directly under so as to be 5 m distant from the installation position of invisible light sensor NVSS in detection area K, if person HM having a body height of 165 cm is projected within an angle of view of puddle WT3, since puddle WT3 becomes a shade of person HM, puddle WT3 is not able to be detected. Invisible light sensor NVSS can detect that a distance between invisible light sensor NVSS and person HM is 10 m.

In other words, since it is considered that person HM moves within detection area K, if person HM is projected within a detection angle of view of puddle WT3 after surface irradiation (projection) of puddle WT3 which is the measuring target substance (specific substance) with reference light LS1 and measuring light LS2 is started, invisible light sensor NVSS erroneously detects puddle WT3. Accordingly, if invisible light sensor NVSS does not perform the surface irradiation (projection) of detection area K with reference light LS1 and measuring light LS2 at high speed, it is considered that puddle WT3 which is the measuring target substance (specific substance) is erroneously detected.

First Exemplary Embodiment

Figure 3:
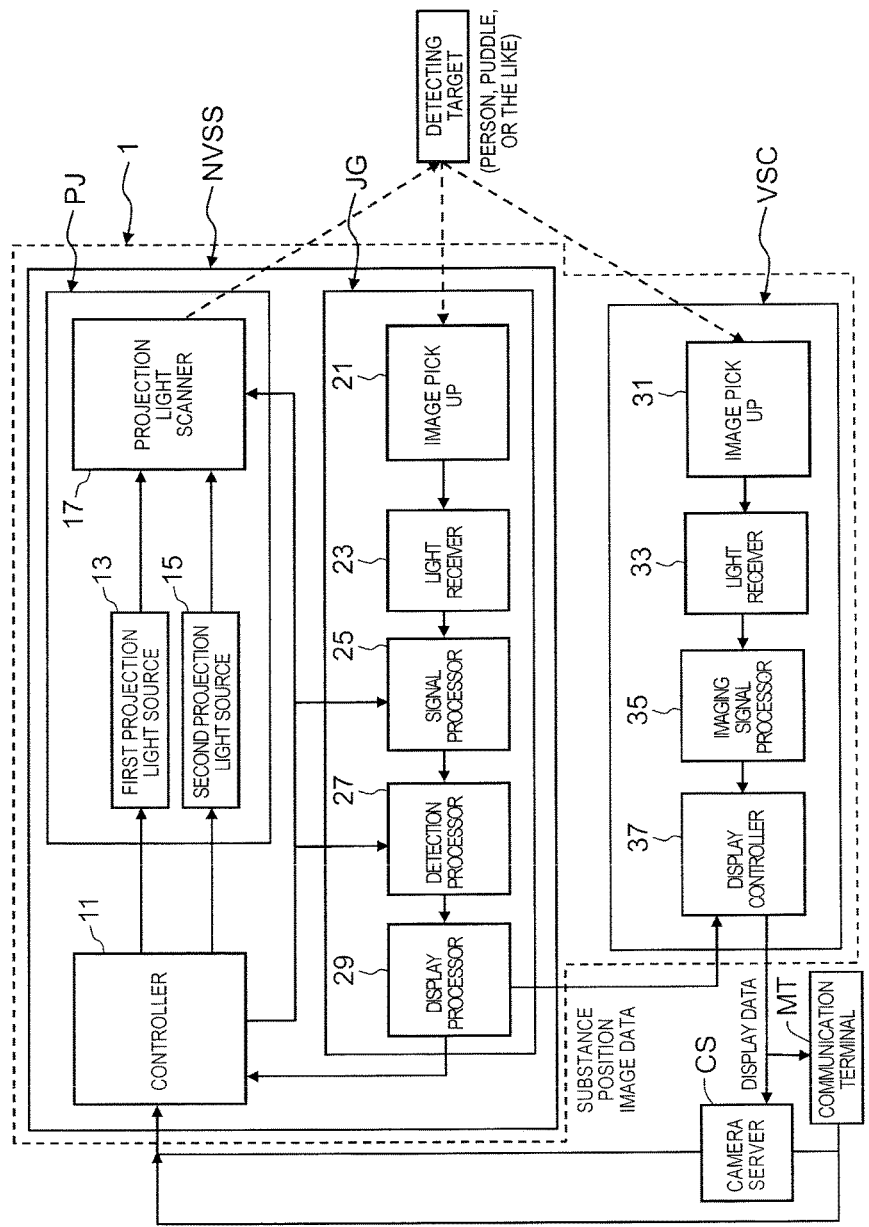
FIG. 3 is a block diagram showing an example of an internal configuration of a detection camera including an invisible light sensor according to a first exemplary embodiment in detail.

FIG. 3 is a block diagram showing an example of an internal configuration of detection camera 1 including invisible light sensor NVSS according to a first exemplary embodiment in detail. Detection camera 1 shown in FIG. 3 includes invisible light sensor NVSS, and visible light camera VSC. Invisible light sensor NVSS includes controller 11, light projector PJ, and image judge JG. Light projector PJ includes first projection light source 13, second projection light source 15, and projection light scanner 17. Image judge JG includes image pick up 21, light receiver 23, signal processor 25, detection processor 27, and display processor 29. Visible light camera VSC includes image pick up 31, light receiver 33, imaging signal processor 35, and display controller 37.

For example, controller 11 is realized using a central processing unit (CPU), a micro processing unit (MPU), or a digital signal processor (DSP), and performs signal processing for managing operation control of the respective components of visible light camera VSC or invisible light sensor NVSS as a whole, a process for inputting and outputting data to and from another components, a process for calculating data, and a process for storing data. Controller 11 includes timing controller 11a to be described below (see FIG. 5).

If controller 11 acquires information of a detecting target distance transmitted through input operation of a user of camera server CS or communication terminal MT, invisible light sensor NVSS calculates a detecting target distance range of the specific substance which is a detecting target from detection camera 1, and sets information of the acquired detecting target distance or the calculated detecting target distance range to signal processor 25 or detection processor 27. Controller 11 sets detection threshold M of the specific substance which is a detecting target of invisible light sensor NVSS to detection processor 27. The details of the operation of controller 11 will be described below with reference to FIG. 18.

Timing controller 11a controls projection timings onto the respective target areas (to be described below) included in detection area K of reference light LS1 from first projection light source 13 and measuring light LS2 from second projection light source 15 for every projection cycle (frame) indicating the surface irradiation of the entire detection area K. The details of projection patterns onto the respective target areas of detection area K of reference light LS1 and measuring light LS2 in timing controller 11a will be described below with reference to the drawings. Timing controller 11a outputs timing signal TR for light scanning shown in FIG. 5 to first projection light source 13 in a case where reference light LS1 is projected from first projection light source 13, and outputs timing signal TR for light scanning to second projection light source 15 in a case where measuring light LS2 is projected from second projection light source 15.

Timing controller 11a outputs light output signal RF to first projection light source 13 when reference light LS1 is projected from first projection light source 13. Light output signal RF, as a signal (reference signal) indicating a start timing at the time of the measurement of the distance between invisible light sensor NVSS and the specific substance, is also input to distance/substance detection processor 27a of detection processor 27.

First projection light source 13 as an example of first light source projects reference light LS1 (for example, infrared light) which is invisible light having a first predetermined wavelength (for example, 1.1 μm) onto the target area of detection area K through surface irradiation using optical scanning by using projection light scanner 17 in response to input of timing signal TR for light scanning from timing controller 11a. As stated above, in the respective exemplary embodiments including the present exemplary embodiment, reference light LS1 projected from first projection light source 13 is used for measuring a distance between invisible light sensor NVSS and the specific substance.

Similarly to measuring light LS2 projected from second projection light source 15, reference light LS1 may be used for detecting the specific substance depending on properties of the specific substance which is the measuring target substance. That is, invisible light sensor NVSS may measure the distance between invisible light sensor NVSS and the specific substance by using reference light LS1 having one kind of wavelength, and may determine whether or not the specific substance is detected. Accordingly, invisible light sensor NVSS can realize the measurement of the distance between invisible light sensor NVSS and the specific substance and the detection of the specific substance by using first projection light source 13 that projects reference light LS1 having one kind of wavelength. Therefore, it is possible to suppress a rise in manufacturing costs of invisible light sensor NVSS.

Whether or not the specific substance is detected may be determined in comparison with a predetermined threshold. The predetermined threshold may be a previously determined value, may be an arbitrarily set value, or may be a value (for example, a value acquired by adding a predetermined margin to intensity values of the respective reflection light beams of reference light LS1 and measuring light LS2 acquired in a state in which there is no specific substance)

based on the intensities of the respective reflection light beams of reference light LS1 and measuring light LS2 acquired in a state in which there is no specific substance. That is, whether or not the specific substance is detected may be determined by comparing the substance position image data acquired in a state in which there is no specific substance with the subsequently acquired substance position image data. As mentioned above, the intensities of the respective reflection light beams of reference light LS1 and measuring light LS2 in a state in which there is no specific substance are acquired, and thus, a threshold appropriate for an installation environment of invisible light sensor NVSS may be set as a threshold for detecting whether or not there is the specific substance.

Second projection light source 15 as an example of a second light source projects measuring light LS2 (for example, infrared light) which is invisible light having a second predetermined wavelength (for example, 1.45 μm) different from the first wavelength onto a target area of detection area K through surface irradiation using optical scanning by using projection light scanner 17 in response to input of timing signal TR for light scanning from timing controller 11a. As described above, in the respective exemplary embodiments including the present exemplary embodiment, measuring light LS2 projected from second projection light source 15 is used for determining whether or not the specific substance is detected in detection area K of invisible light sensor NVSS. The second wavelength of measuring light LS2 which is 1.45 μm is a wavelength appropriate in a case where the specific substance which is the measuring target substance is water (the same is true of water vapor) such as puddle WT (see FIG. 1).

Accordingly, invisible light sensor NVSS measures the distance between invisible light sensor NVSS and the specific substance by using reference light LS1 having the first wavelength and reflection light RV1 thereof, and uses reflection light RV1 of reference light LS1 having the first wavelength, as reference data for detecting the specific substance. Invisible light sensor NVSS determines whether or not the specific substance is detected in detection area K by using reflection light RV2 of measuring light LS2 having the second wavelength and the above-described reference data (that is, reflection light RV1 of reference light LS1). Therefore, invisible light sensor NVSS can detect the specific substance in detection area K with high accuracy by using projection light beams having two different kinds of wavelengths and reflection light beams thereof in the measurement of the distance between invisible light sensor NVSS and the specific substance and the detection of the specific substance.

Projection light scanner 17 two-dimensionally scans target areas PT (see FIG. 7) of detection area K of invisible light sensor NVSS with reference light LS1 projected from first projection light source 13 and measuring light LS2 projected from second projection light source 15 through optical scanning, and performs surface irradiation on detection area K. Accordingly, image judge JG can measure the distance between invisible light sensor NVSS and the specific substance by using reflection light RV1 which is reflection light of reference light LS1 from the specific substance, and can determine whether or not the specific substance is detected in detection area K by using reflection light RV2 which is reflection light of measuring light LS2 from the specific substance and reflection light RV1 (that is, reflection light RV1 of reference light LS1) described above.

Figure 4:
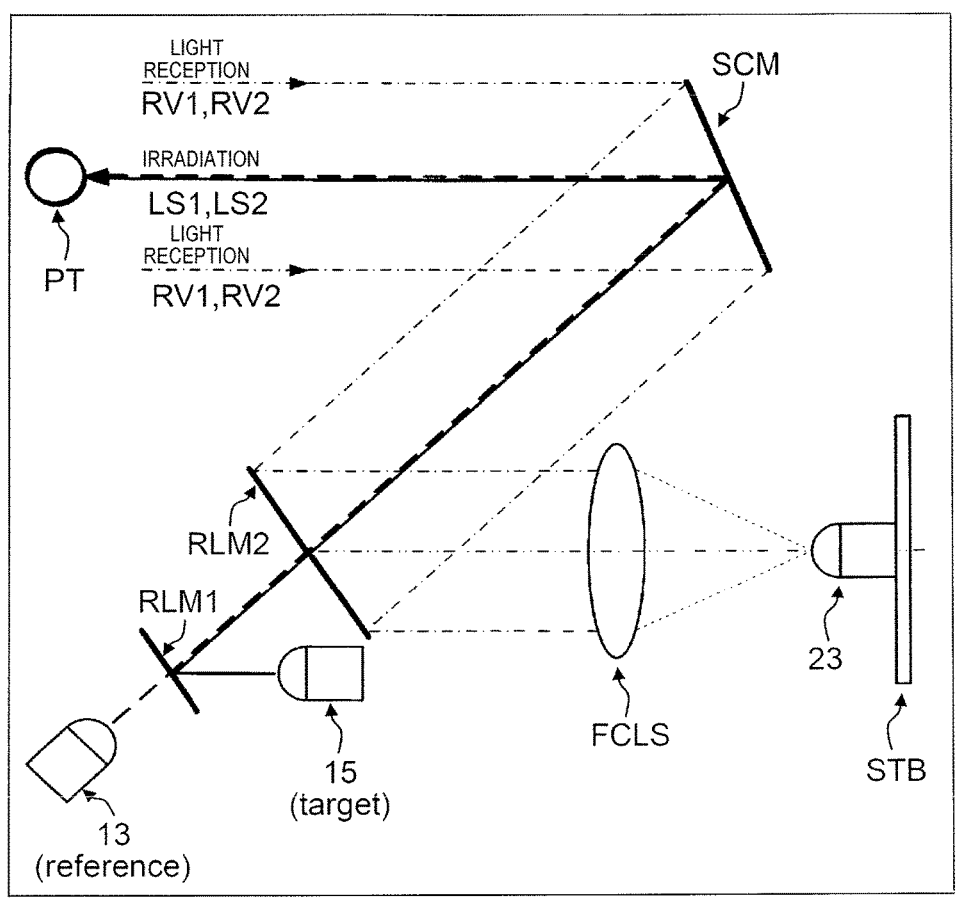
FIG. 4 is a block diagram showing a first configuration example of a projection light scanner and an image pick up related to reflection light and projection of reference light and measuring light of the invisible light sensor in the first exemplary embodiment.

FIG. 4 is a block diagram showing a first configuration example of the projection light scanner and the image pick up related to reflection light and the projection of the reference light and the measuring light of the invisible light sensor in the first exemplary embodiment. For example, projection light scanner 17 includes at least reflection mirrors RLM1 and RLM2 and scanning mirror SCM shown in FIG. 4.

In FIG. 4, reference light LS1 projected (output) from first projection light source 13 passes (penetrates) through reflection mirrors RLM1 and RLM2, and is incident on scanning mirror SCM on which scanning control is performed by a stepping motor (not shown) at a predetermined incidence angle so as to be applied to target area PT of the corresponding projection position (irradiation position) of detection area K. Reference light LS1 is reflected from scanning mirror SCM at a reflection angle equal to the incidence angle, and is applied to desired target area PT.

Measuring light LS2 projected (output) from second projection light source 15 is reflected from reflection mirror RLM1, passes (penetrates) through reflection mirror RLM2, and then is incident on scanning mirror SCM on which scanning control is performed by stepping motor (not shown) at a predetermined incidence angle so as to be applied to target area PT of the corresponding projection position (irradiation position) of detection area K. Measuring light LS2 is reflected from scanning mirror SCM at a reflection angle equal to the incidence angle, and is applied to desired target area PT.

Reflection mirror RLM1 is previously disposed such that reference light LS1 from first projection light source 13 passes and measuring light LS2 from second projection light source 15 is reflected so as to be projected onto reflection mirror RLM2. Reflection mirror RLM2 is previously disposed such that both of reference light LS1 and measuring light LS2 pass and both of reflection light beams RV1 and RV2 are reflected so as to be projected onto condenser lens FCLS. The scanning control is performed on scanning mirror SCM by the stepping motor (not shown) such that reference light LS1 or measuring light LS2, or both of them is able to be sequentially projected onto target area PT of detection area K, and the scanning mirror is previously disposed such that reflect reflection light beams RV1 and RV2 are reflected and projected onto reflection mirror RLM2.

Figure 5:
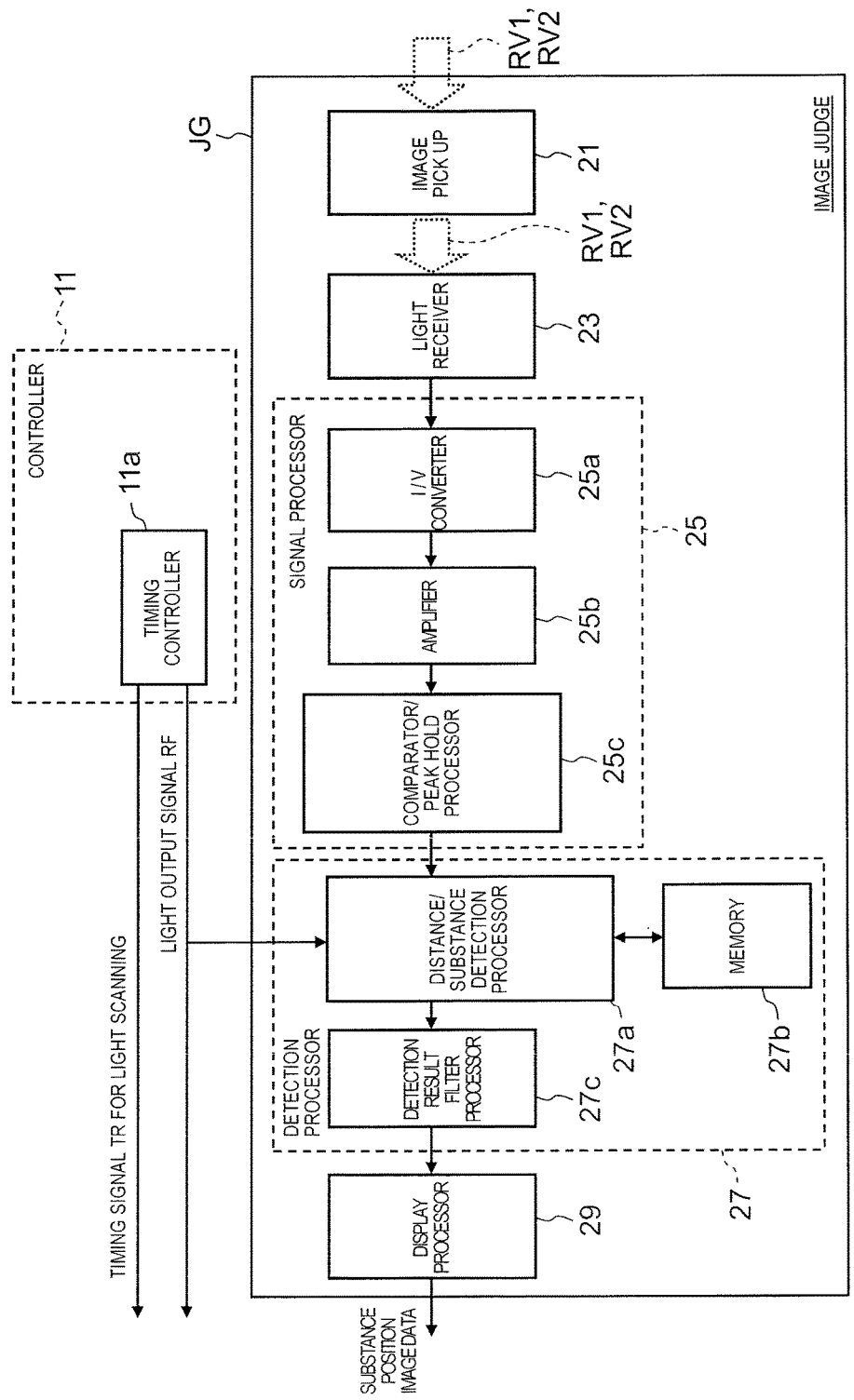
FIG. 5 is a block diagram showing an example of an internal configuration of an image judge of the invisible light sensor according to the first exemplary embodiment in detail.

Hereinafter, an internal configuration of image judge JG will be described in detail with reference to FIGS. 3 to 5. FIG. 5 is a block diagram showing an example of the internal configuration of image judge JG of invisible light sensor NVSS according to the first exemplary embodiment in detail.

For example, image pick up 21 is realized using condenser lens FCLS shown in FIG. 4, and concentrates reflection light beams RV1 and RV2 which are reflection light beams of the light beams (for example, reflection light beams RV1 and RV2) incident on invisible light sensor NVSS from scanning mirror SCM and reflection mirror RLM2, and forms an image of reflection light beams RV1 and RV2 on a predetermined imaging surface of light receiver 23 disposed on circuit board SBT.

Light receiver 23 is an image sensor having a peak of spectral sensitivity to wavelengths of both reference light LS1 and measuring light LS2. Light receiver 23 converts an optical image of reflection light RV1 or reflection light RV2 which is formed on the imaging surface into an electrical signal. An output of light receiver 23 is input, as the electrical signal (for example, current signal), to signal processor 25. Image pick up 21 and light receiver 23 have a function of an imager of invisible light sensor NVSS.

Signal processor 25 includes I/V converter 25a, amplifier 25b, and comparator/peak hold processor 25c. I/V converter 25a converts a current signal which is an output signal (analog signal) of light receiver 23 into a voltage signal. Amplifier 25b amplifies a level of the voltage signal which is an output signal (analog signal) of I/V converter 25a up to a level that is able to be processed by comparator/peak hold processor 25c.

Comparator/peak hold processor 25c performs binarization of an output signal of amplifier 25b depending on the comparison result of the output signal (analog signal) of amplifier 25b with a predetermined threshold, and outputs the binarized signal to distance/substance detection processor 27a. Comparator/peak hold processor 25c includes an analog-to-digital converter (ADC), detects a peak of the analog-to-digital (AD) conversion result of the output signal (analog signal) of amplifier 25b, retains the detected peak, and outputs information of the peak to distance/substance detection processor 27a.

Detection processor 27 as an example of a substance detector includes distance/substance detection processor 27a, memory 27b, and detection result filter 27c. Distance/substance detection processor 27a measures the distance between invisible light sensor NVSS and the specific substance based on the output (binarized signal) of reflection light RV1 of reference light LS1 having the first wavelength (for example, 1.1 µm) from comparator/peak hold processor 25c.

Figures 19A, 19B:
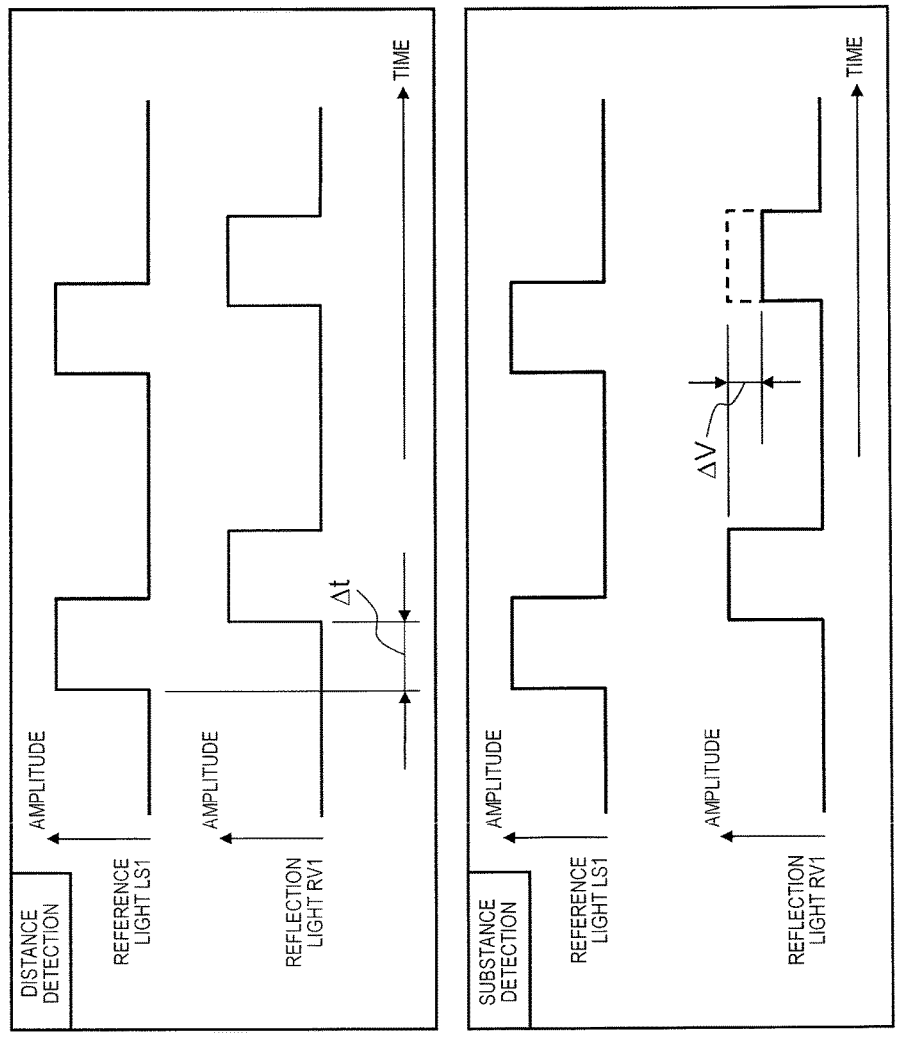
FIG. 19A is a principle explanatory diagram of distance detection using reference light having one kind of wavelength in the invisible light sensor according to the first exemplary embodiment.
FIG. 19B is a principle explanatory diagram of substance detection using reference light having one kind of wavelength in the invisible light sensor according to the first exemplary embodiment.

Specifically, distance/substance detection processor 27a measures the distance between invisible light sensor NVSS and the specific substance based on time difference Δt (see FIG. 19A or 20A) between a time when reference light LS1 is projected and a time when reflection light RV1 is received. FIG. 19A is a principle explanatory diagram of the distance detection using reference light LS1 having one kind of wavelength in invisible light sensor NVSS according to the first exemplary embodiment. FIG. 20A is a principle explanatory diagram of the distance detection using reference light LS1 having the first wavelength of different two kinds of wavelengths in invisible light sensor NVSS according to the first exemplary embodiment.

Distance/substance detection processor 27a determines an input time of light output signal RF from timing controller 11a as a projection time of reference light LS1, and determines an input time of the output from comparator/peak hold processor 25c as a reception time of reflection light RV1. For example, distance/substance detection processor 27a calculates the distance using "distance=light velocity× (time difference Δt/2), and thus, the distance between invisible light sensor NVSS and the specific substance is easily acquired. In the measurement of the distance in distance/substance detection processor 27a, the output of reflection light RV1 of reference light LS1 having at least one kind of wavelength from comparator/peak hold processor 25c is required. Distance/substance detection processor 27a outputs information of the distance as the calculation result to detection result filter 27c.

Distance/substance detection processor 27a determines whether or not the specific substance is detected in detection area K based on the output (information of the peak) of reflection light RV1 of reference light LS1 having the first wavelength from comparator/peak hold processor 25c to target area PT in detection area K and the output (information of the peak) of reflection light RV2 of measuring light LS2 having the second wavelength from comparator/peak hold processor 25c to target area PT of detection area K.

Specifically, for example, in a case where the same target area PT in detection area K is irradiated with reference light LS1 and measuring light LS2, distance/substance detection processor 27a temporarily stores the output (information of the peak) of reflection light RV1 of reference light LS1 from comparator/peak hold processor 25c in memory 27b, and waits for the output (information of the peak) of reflection light RV2 of measuring light LS2 from comparator/peak hold processor 25c to be acquired. After the output (information of the peak) from comparator/peak hold processor 25c in reflection light RV2 of measuring light LS2 is acquired, distance/substance detection processor 27a compares the output (information of the peak) of reflection light RV1 of reference light LS1 from comparator/peak hold processor 25c with the output (information of the peak) of reflection light RV2 of measuring light LS2 from comparator/peak hold processor 25c in the same target area PT of detection area K by referring to memory 27b.

In a case where the same target area PT of detection area K is not irradiated with reference light LS1 and measuring light LS2, distance/substance detection processor 27a estimates intensity of reflection light RV1 of reference light LS1 in a case where target position PT which is not irradiated with reference light LS1 is irradiated with reference light LS1 through a predetermined interpolation process (to be described below) by using the intensity (the output (information of the peak) from comparator/peak hold processor 25c) of reflection light RV1 of reference light LS1 applied to target area PT near target area PT irradiated with measuring light LS2. Distance/substance detection processor 27a compares the interpolation process result (that is, the intensity of reflection light RV1 of reference light LS1 in a case where target position PT which is not irradiated with reference light LS1 is irradiated with reference light LS1) with the intensity of reflection light RV2 of measuring light LS2.

For example, in a case where there is puddle WT in target area PT, since measuring light LS2 having the second wavelength (for example, 1.45 µm) applied to target area PT is absorbed, the intensity (amplitude) of reflection light RV2 of measuring light LS2 is attenuated (see FIGS. 19B and 20B). FIG. 19B is a principle explanatory diagram of the substance detection using reference light LS1 having one kind of wavelength in invisible light sensor NVSS according to the first exemplary embodiment. FIG. 20B is a principle explanatory diagram of the substance detection using reference light LS1 and measuring light LS2 having two different kinds of wavelengths in invisible light sensor according to the first exemplary embodiment. Accordingly, distance/substance detection processor 27a can determine whether or not the specific substance is detected in detection area K based on the comparison result (that is, time difference ΔV between the respective amplitudes or the respective intensities of reflection light RV1 and reflection light RV2) for each same target area PT of detection area K. Distance/substance detection processor 27a may determine whether or not the specific substance is detected in detection area K based on the comparison result of the adjacent target areas PT instead of the comparison result of each same target area PT in detection area K.

Distance/substance detection processor 27a may determine whether or not the specific substance is detected in detection area K according to comparison of ratio R between the calculated amplitude difference and amplitude VA, which is acquired by calculating amplitude difference (VA-VB) between amplitude VA of reflection light RV1 of reference light LS1 having the first wavelength and amplitude VB of reflection light RV2 of measuring light LS2 having the second wavelength, with a predetermined threshold M in magnitude (see FIG. 21). FIG. 21 is an outline explanatory diagram of the substance detection in the invisible light sensor according to the first exemplary embodiment. For example, distance/substance detection processor 27a determines that puddle WT is detected if R>M, and determines that puddle WT is not detected if R≤M. As stated above, distance/substance detection processor 27a can exclude influence of noise (for example, disturbance light) and can determine whether or not the specific substance is detected with high accuracy by determining whether or not the specific substance is detected in detection area K according to the comparison result of ratio R between amplitude difference (VA−VB) and amplitude VA with threshold M.

For example, memory 27b is realized using a random access memory (RAM), and temporarily stores the output (information of the peak) of reflection light RV1 of reference light LS1 from comparator/peak hold processor 25c or data of the interpolation process result described above.

Detection result filter 27c filters information related to the specific substance of which the distance from invisible light sensor NVSS in detection area K is within a predetermined detecting target distance or the detecting target distance range designated from controller 11 based on the output from distance/substance detection processor 27a and information of the detecting target distance or detecting target distance range, and extracts the filtered information. Detection result filter 27c outputs information related to the extraction result in detection area K to displayer processor 29. For example, detection result filter 27c outputs information related to the detection result of the specific substance on the floor (distance=5 m, see FIG. 2) in the detection area to display processor 29.

Display processor 29 generates, as an example of the information related to the specific substance of which the distance from invisible light sensor NVSS within detection area K is within the detecting target distance or the detecting target distance range, substance position image data indicating the position of the specific substance in detection area K of each distance from invisible light sensor NVSS by using the output of detection result filter 27c. Display processor 29 outputs substance position image data including the information of the distance between invisible light sensor NVSS and the specific substance to display controller 37 of visible light camera VSC. In the respective exemplary embodiments including the present exemplary embodiment, display processor 29 may transmit the substance position image data to display controller 37 of visible light camera VSC, or may transmit the substance position image data to, for example, monitor MNT, camera server CS, or communication terminal MT to be described below. Accordingly, since invisible light sensor NVSS combines information related to the specific substance acquired by detection processor 27 with visible light image data of detection area K and displays the combined data, it is possible to convincingly demonstrate where the specific substance is present in each detection area K to the user.

For example, image pick up 31 is configured using the condenser lens, concentrates light (for example, reflection light RV0 which is visible light) incident from the outside with the inside of detection area K of visible light camera VSC as an angle of view, and forms an image of reflection light RV0 on a predetermined imaging surface of light receiver 33.

Light receiver 33 is an image sensor having a peak of spectral sensitivity to a wavelength (for example, 0.4 μm to 0.7 μm) of visible light. Light receiver 33 converts an optical image formed on the imaging surface into an electrical signal. The output of light receiver 33 is input, as the electrical signal, to imaging signal processor 35. Image pick up 31 and light receiver 33 have a function of an imager of visible light camera VSC.

Imaging signal processor 35 generates visible light image data defined by YUV (luminance and chrominance) or red, green and blue (RGB) capable of being recognized by a person by using the electrical signal which is the output of light receiver 33. Accordingly, the visible light image data imaged by visible light camera VSC is formed. Imaging signal processor 35 outputs the visible light image data to display controller 37.

In a case where the specific substance is detected in a predetermined position of the visible light image data by using the visible light image data output from imaging signal processor 35 and the substance position image data output from display processor 29, display controller 37 generates, as an example of the information related to the specific substance, display data acquired by a process of combining the visible light image data with the substance position image data.

In a case where the distance between invisible light sensor NVSS and the specific substance is within the detecting target distance or the detecting target distance range, display controller 37 generates, as an example of the information related to the specific substance, display data acquired by performing the process of combining the visible light image data with the substance position image data. For example, display controller 37 transmits the display data to camera server CS or communication terminal MT connected via a network, and prompts the camera server or the communication terminal to display the display data.

Controller 11 may change the detecting target distance or the detecting target distance range as an example of setting distance information set by detection processor 27. The change of the detecting target distance range may be automatically performed by controller 11, or may be performed by the user using communication terminal MT at an arbitrary timing. Accordingly, controller 11 can set an appropriate detecting target distance or detecting target distance range depending on an installation environment of invisible light sensor NVSS. For example, the setting distance information is a detecting target distance previously set by detection result filter 27c of detection processor 27.

In a case where controller 11 calculates the detecting target distance range based on information of the detecting target distance input by camera server CS or communication terminal MT, a value of the detecting target distance range calculated may be changed depending on a value of the detecting target distance. In a case where the distance up to the detecting target is long, since the attenuation of the intensity (or amplitude) of the reflection light is greater than that in a case where the distance up to the detecting target is short, an error when distance/substance detection processor 27a detects the distance is large. Preferably, the greater the value of the input detecting target distance, the greater the detecting target distance range calculated by controller 11. For example, in a case where the detecting target distance output from controller 11 is 3 m, detection processor 27 changes the detecting target distance range to a range of 2 to 4 m. In a case where the detecting target distance output from controller 11 is 100 m, detection processor 27 changes the detecting target distance range to a range of 95 to 105 m. Accordingly, invisible light sensor NVSS can set an appropriate detecting target distance range depending on the distance up to the specific substance. Therefore display controller 37 can generate the display data as an example of the information related to the specific substance in consideration of the error when detection processor 27 detects the distance, which corresponds to a length of the detecting target distance. Detection camera 1 can detect the specific substance by setting the detecting target distance range even in a case where the distance between the specific substance and detection camera 1 does not completely match to the detecting target distance output from controller 11.

Camera server CS transmits the display data output from display controller 37 to communication terminal MT or one or more external connection devices (not shown), and prompts communication terminal MT or one or more external connection devices to display the display data on a display screen. Camera server CS transmits the information of the detecting target distance or the detecting target distance range of the specific substance transmitted through an input operation of the user of communication terminal MT or one or more external connection devices to detection camera 1. The information of the detecting target distance or the detecting target distance range of the specific substance is input to controller 11. Accordingly, camera server CS can input the information of the detecting target distance or the detecting target distance range of the specific substance designated by the input operation of the user to invisible light sensor NVSS. The detecting target distance range of the specific substance input to invisible light sensor NVSS from camera server CS may be in plural in number, and the setting numbers of the plurality of detecting target distance ranges may also be arbitrarily input. Accordingly, camera server CS can arbitrarily set a detecting target distance range desired by the user or the setting number of the detecting target distance range to invisible light sensor NVSS.

For example, communication terminal MT is a portable communication terminal used by an individual user, receives the display data transmitted from display controller 37 via a network (not shown), and displays the display data on a display screen (not shown) of communication terminal MT. In a case where the information of the detecting target distance of the specific substance is input through the input operation of the user, communication terminal MT transmits the information of the detecting target distance or the detecting target distance range of the specific substance to invisible light sensor NVSS via camera server CS or directly transmits this information. Similarly, the information of the detecting target distance or the detecting target distance range of the specific substance is input to controller 11. Accordingly, communication terminal MT can input the information of the detecting target distance or the detecting target distance range of the specific substance designated through the input operation of the user to invisible light sensor NVSS via camera server CS or directly transmit this information. The detecting target distance range of the specific substance input to invisible light sensor NVSS from communication terminal MT may be a plurality of ranges, and the setting numbers of the plurality of detecting target distance ranges may be arbitrarily input. Accordingly, communication terminal MT can arbitrarily set a detecting target distance range desired by the user or the setting number of the detecting target distance range to invisible light sensor NVSS.

In a case where the detecting target distance range is input through the input operation of the user, controller 11 may set the input detecting target distance range to detection processor 27 without changing this range. Controller 11 may calculate the detecting target distance range set by detection processor 27 and may set the calculated range to detection processor 27 based on the input detecting target distance range. For example, in a case where 4 to 7 m is input as the detecting target range through the input operation of the user, controller 11 may change the detecting target distance range to a range of 5 to 6 m or 3 to 8 m, and may set the changed range to detection processor 27.

(Description of Example of Initial Operation in Invisible Light Sensor)

Figure 18:
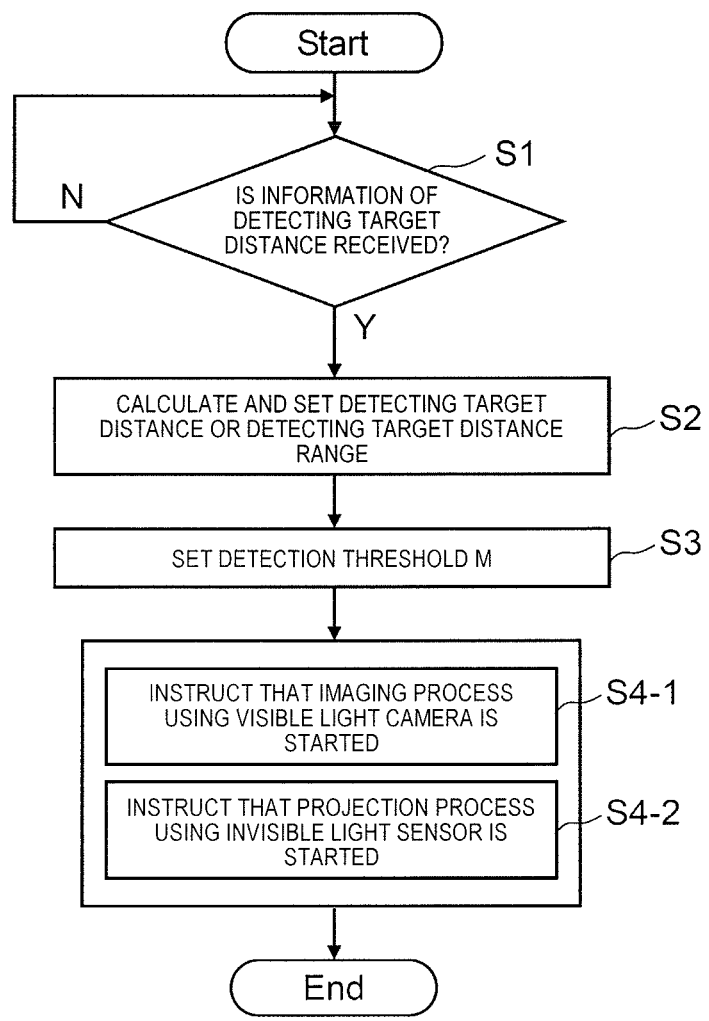
FIG. 18 is a flowchart showing an example of an initial operation in a controller of the invisible light sensor according to the first exemplary embodiment.

Hereinafter, an example of an initial operation in controller 11 of invisible light sensor NVSS according to the present exemplary embodiment will be described with reference to FIG. 18. FIG. 18 is a flowchart showing an example of the initial operation in controller 11 of invisible light sensor NVSS according to the first exemplary embodiment.

In FIG. 18, in a case where invisible light sensor NVSS receives the information of the detecting target distance of the specific substance transmitted from camera server CS or communication terminal MT (S1, Y), controller 11 acquires the information of the detecting target distance of the specific substance. Controller 11 calculates the detecting target distance range of the specific substance as the detecting target of invisible light sensor NVSS based on the information of the detecting target distance of the specific substance, and sets the information of the acquired detecting target distance or the calculated detecting target distance range to signal processor 25 or detection processor 27 (S2).

For example, the information of the detecting target distance includes information of the distance or direction from invisible light sensor NVSS as the detecting target which is the specific substance present within detection area K, or installation condition information of invisible light sensor NVSS. The information of the distance from invisible light sensor NVSS may be a previously determined value, or may be arbitrarily set by the user who uses communication terminal MT. The installation condition information of invisible light sensor NVSS may be previously set to invisible light sensor NVSS, or may be arbitrarily set by the user who uses communication terminal MT. For example, the installation condition information includes information of a height (5 m shown in FIG. 2) of invisible light sensor NVSS from a predetermined surface (for example, floor surface), a projection angle (for example, an angle formed by the floor surface and a projection direction of reference light LS1 or measuring light LS2 output from projection light scanner 17) of invisible light sensor NVSS, and an area of a living room where the invisible light camera is installed). For example, in invisible light sensor NVSS to which the installation condition information is input, controller 11 may calculate the detecting target distance or the detecting target distance range based on the installation condition information of the specific substance. Invisible light sensor NVSS can detect the specific substance depending on the installation environment and can suppress erroneous detection by setting such installation condition information.

Controller 11 may change the detecting target distance range calculated in step S2 depending on the information the height of invisible light sensor NVSS from a predetermined surface (for example, floor surface). The change of the detecting target distance range may be automatically performed by controller 11, or may be performed by the user using communication terminal MT at an arbitrary timing. The detecting target distance range may not be calculated based on the detecting target distance, and may be directly input by camera server CS or communication terminal MT. Alternatively, invisible light sensor NVSS may be provided with an input capable of inputting the detecting target distance or the detecting target distance range.

In a case where the distance up to the detecting target is long, since the attenuation of the intensity (or amplitude) of the reflection light is greater than that in a case where the distance from the detecting target is short, an error when distance/substance detection processor 27a detects the distance is large. Thus, preferably, the greater the information of the input height, the greater the detecting target distance range calculated by controller 11. Accordingly, invisible light sensor NVSS changes the detecting target distance range depending on a case where the information of the height of invisible light sensor NVSS from a predetermined surface is low (for example, 3 m) or a case where this information is high (for example, 100 m), and thus, it is possible to further improve detection accuracy of the specific substance in invisible light sensor NVSS in consideration of the error when invisible light sensor NVSS detects the distance. Display controller 37 can generate the display data as an example of the information related to the specific substance in consideration of the error when the detection processor 27 detects the distance depending on the height with which invisible light sensor NVSS is installed.

Controller 11 sets detection threshold M of the specific substance in detection processor 27 of invisible light sensor NVSS to distance/substance detection processor 27a of detection processor 27 (S3). Preferably, detection threshold M is appropriately set depending on the specific substance as the detecting target.

After step S3, controller 11 outputs a control signal for starting an imaging process to each component, of visible light camera VSC (S4-1), and outputs timing signal TR for light scanning for causing first projection light source 13 or second projection light source 15 to start to project reference light LS1 or measuring light LS2 to first projection light source 13 and second projection light source 15 of invisible light sensor NVSS (S4-2). Any one of the operation of step S4-1 and the operation of step S4-2 may be performed at a timing earlier than that of the other one.

(Operation Outline of Invisible Light Sensor According to Present Exemplary Embodiment)

Figure 6:
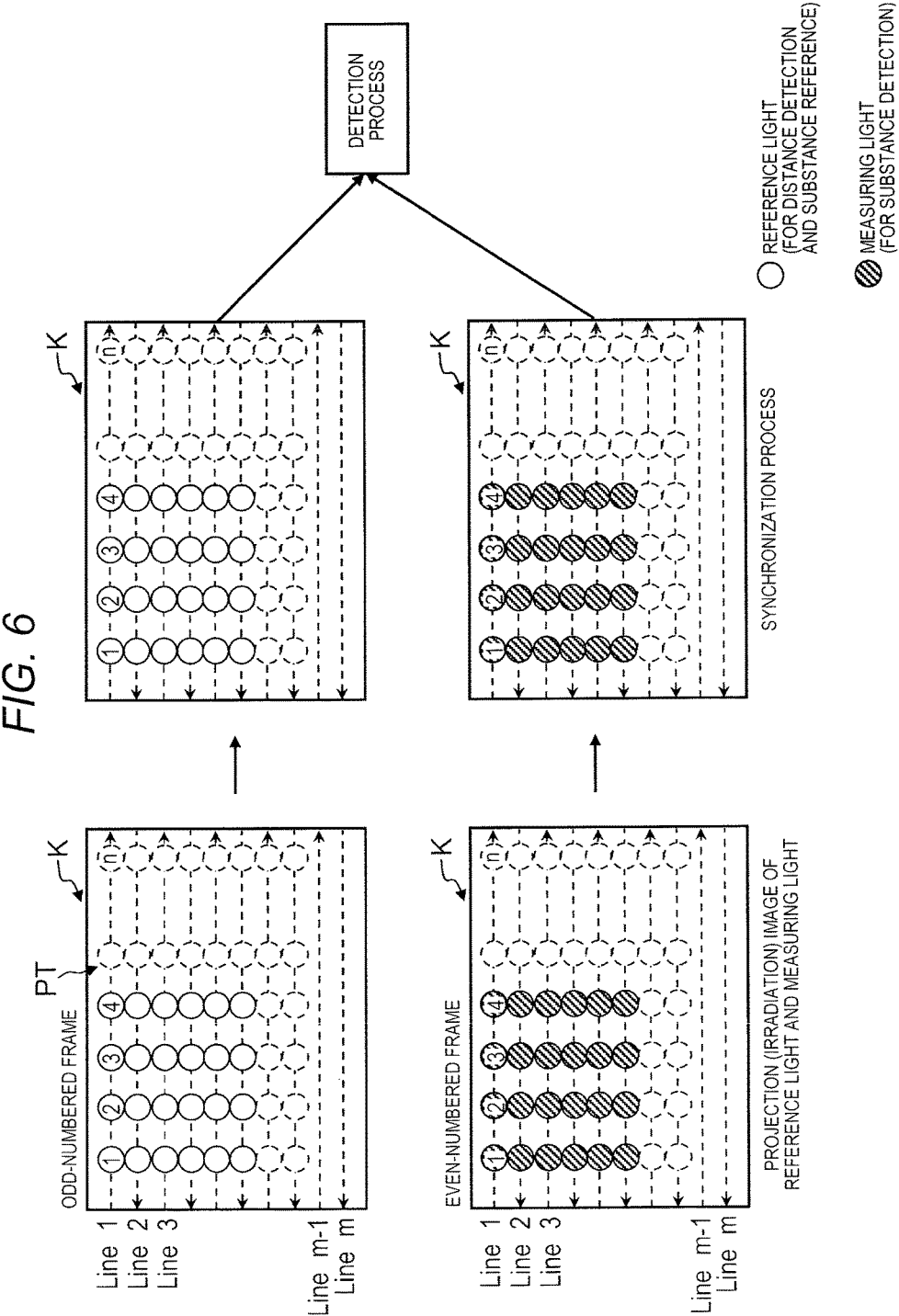
FIG. 6 is an explanatory diagram showing examples of projection (irradiation) images of a first projection light source and a second projection light source according to a comparative example.
Figure 7:
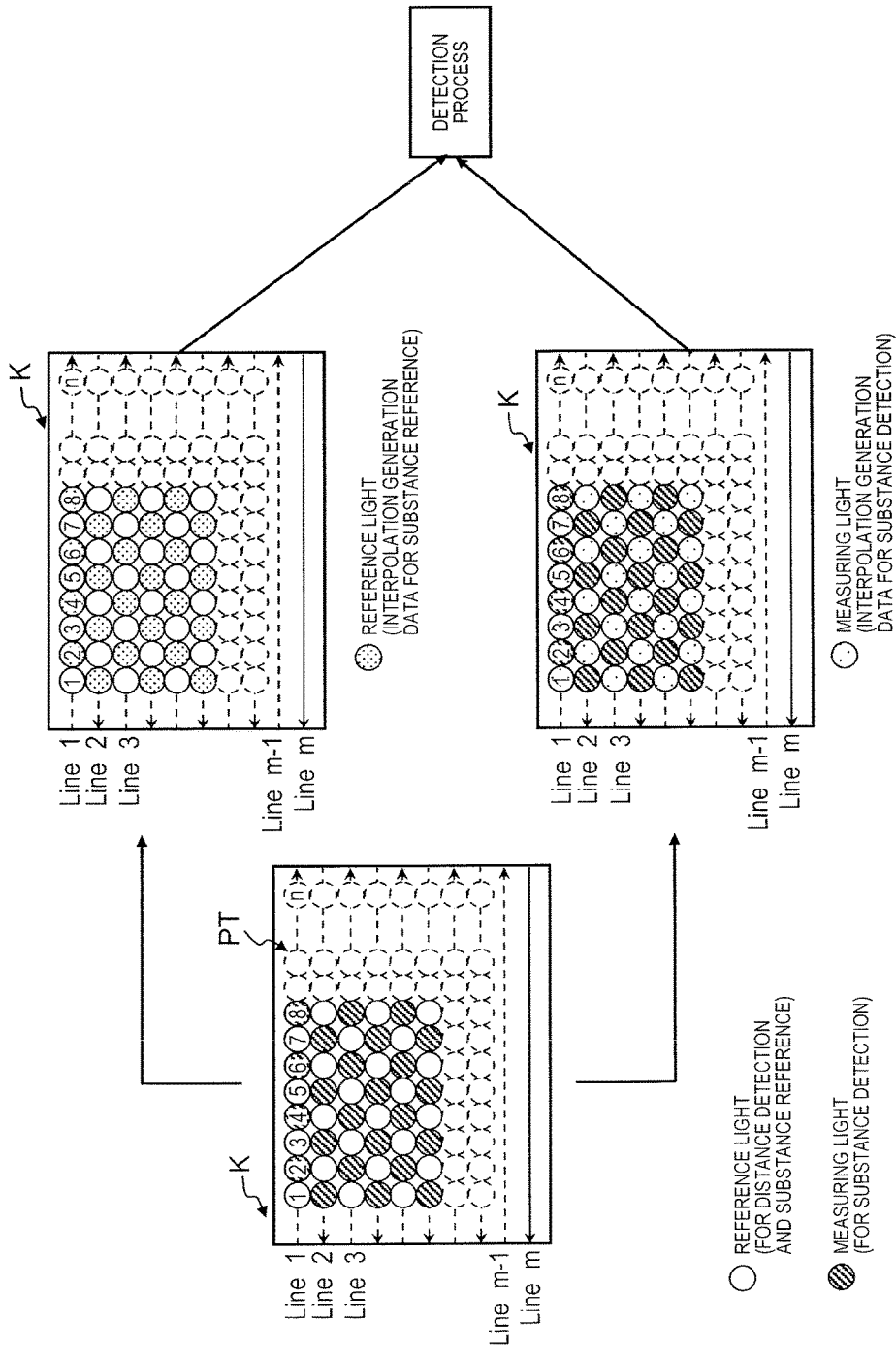
FIG. 7 is an explanatory diagram showing an example of the projection (irradiation) images of the first projection light source and the second projection light source according to the first exemplary embodiment.

Hereinafter, the operation outline of invisible light sensor NVSS according to the present exemplary embodiment will be described with reference to FIGS. 6 and 7. FIG. 6 is an explanatory diagram showing examples of projection (irradiation) images of first projection light source 13 and second projection light source 15 according to a comparative example. FIG. 7 is an explanatory diagram showing examples of projection (irradiation) images of first projection light source 13 and second projection light source 15 according to the first exemplary embodiment.

Initially, in the comparative example shown in FIG. 6, invisible light sensor NVSS discretely applies reference light LS1 to target areas PT of detection area K in a horizontal direction from first projection light source 13 in odd-numbered frames. Here, since detection area K includes n numbers of target areas in the horizontal direction and m numbers of target areas in a vertical direction, the detection area includes a total of n×m numbers of target areas. Each target area PT has a size corresponding to a single pixel of the visible light image data acquired through the imaging of visible light camera VSC. n and m are integers which are equal to or greater than 2. Invisible light sensor NVSS discretely applies measuring light LS2 to target areas PT of detection area K in the horizontal direction from second projection light source 15 in even-numbered frames. Arrows of FIG. 6 indicate that reference light LS1 and measuring light LS2 is sequentially applied in a direction in which the arrows proceed.

Invisible light sensor NVSS aligns reflection light RV1 of reference light LS1 and reflection light RV2 of measuring light LS2 in each same target area PT of detection area K acquired in the odd-numbered frames and the even-numbered frames (synchronization process), and determines whether or not the presence or absence of the specific substance is detected in each target area PT by using reflection light RV1 of reference light LS1 and reflection light RV2 of measuring light LS2 in the same target area PT (detection process). In FIG. 6, about 10 seconds are necessary for one frame (that is, time necessary for surface irradiation of detection area K with reference light LS1 or measuring light LS2). About 5 seconds are necessary for surface irradiation, and about 5 seconds are necessary for reception of reflection light.

Accordingly, in the comparative example shown in FIG. 6, since the application of measuring light LS2 is started after reference light LS1 is completely applied to whole target areas PT of detection area K, a time difference between an application timing of reference light LS1 and an application timing of measuring light LS2 is about 10 seconds equivalent to one frame, and thus, a status of detection area K is changed during about 10 seconds. Therefore, the erroneous detection of the specific substance is highly likely to be caused.

Meanwhile, in the present exemplary embodiment shown in FIG. 7, for example, invisible light sensor NVSS switches between reference light LS1 and measuring light LS2 to irradiate target area PT adjacent to detection area K in the horizontal direction in a time-division manner. Invisible light sensor NVSS separates reference-light acquisition data indicating the intensity of reflection light RV1 in each target area PT irradiated with reference light LS1 and measuring-light acquisition data indicating the intensity of reflection light RV2 in each target area PT irradiated with measuring light LS2, and performs the above-described interpolation process on these data items. The details of the interpolation process will be described in detail with reference to FIGS. 8 to 10. Invisible light sensor NVSS determines whether or not the presence or absence of the specific substance is detected for each target area PT by using the interpolation process result corresponding to reflection light RV1 of reference light LS1 and the interpolation process result corresponding to reflection light RV2 of measuring light LS2 (detection process).

Accordingly, unlike the comparative example, since a time difference between the application timing of reference light LS1 and the application timing of measuring light LS2 is approximately a time (for example, 20 microseconds) equivalent to as much as one target area PT is irradiated in the present exemplary embodiment shown in FIG. 7, it is difficult to consider that the status of detection area K is changed between the application timing of reference light LS1 and the application timing of measuring light LS2, and thus, invisible light sensor NVSS can further suppress the erroneous detection of the specific substance than that in the comparative example shown in FIG. 6.

(Interpolation Process in Invisible Light Sensor)

Figure 8:
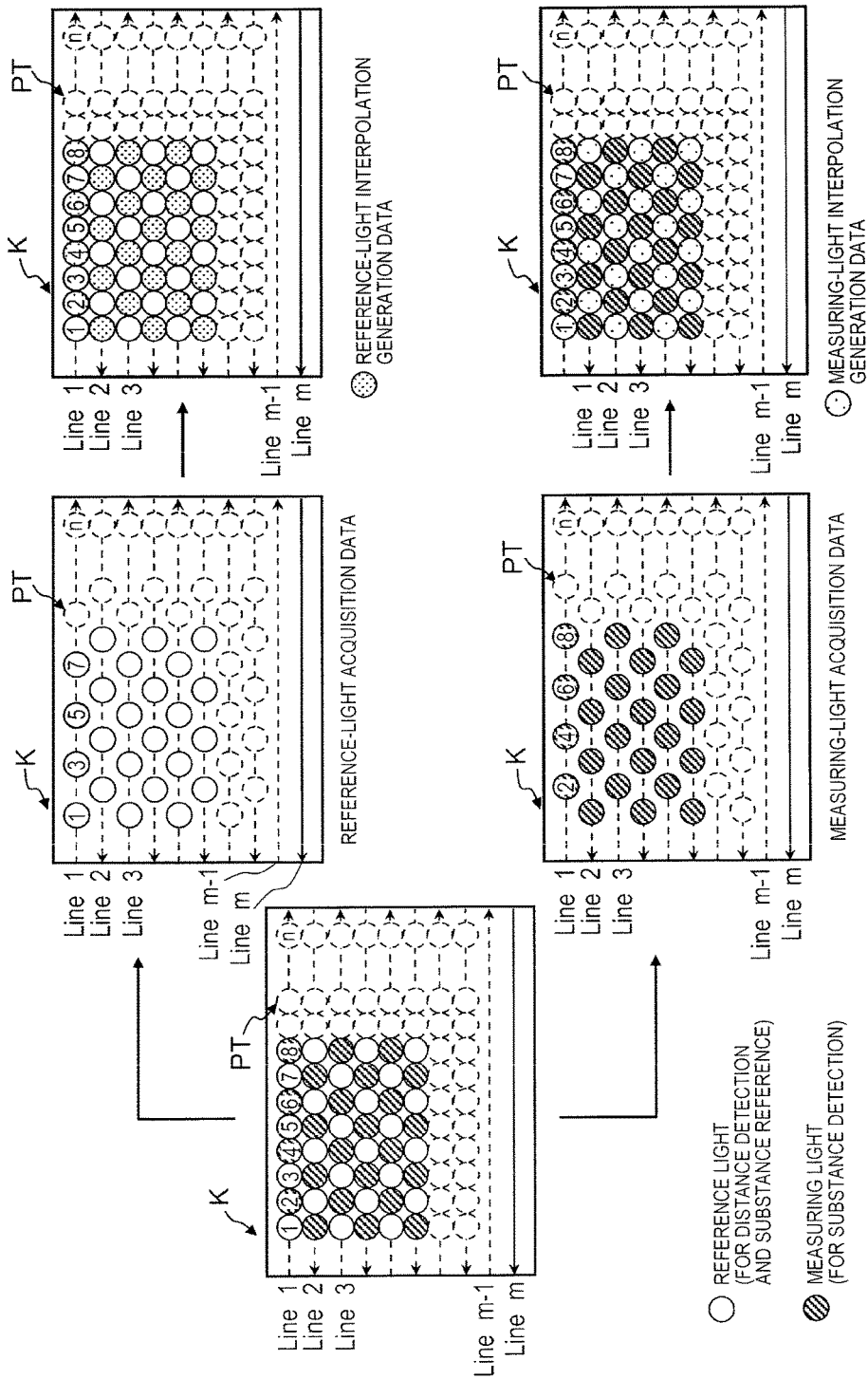
FIG. 8 is a schematic diagram showing an example of an operation outline of an interpolation process in the invisible light sensor according to the first exemplary embodiment.
Figure 9:
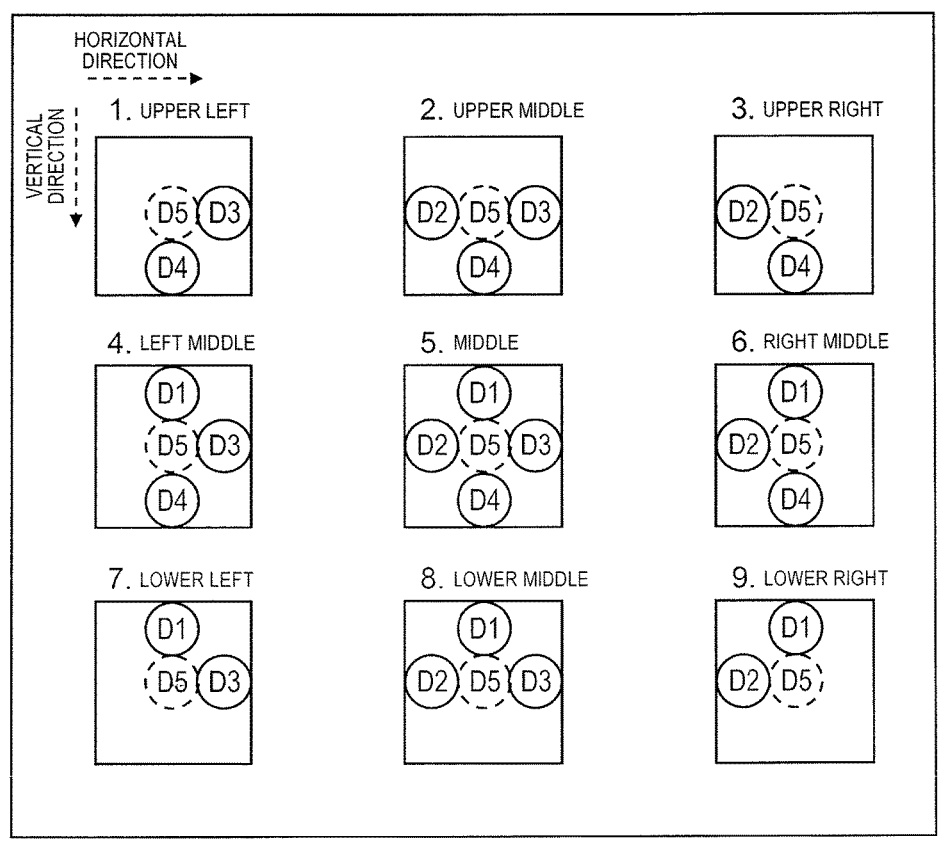
FIG. 9 is a schematic diagram showing a type of the interpolation process on target area (D5) of the interpolation process.
Figure 10:
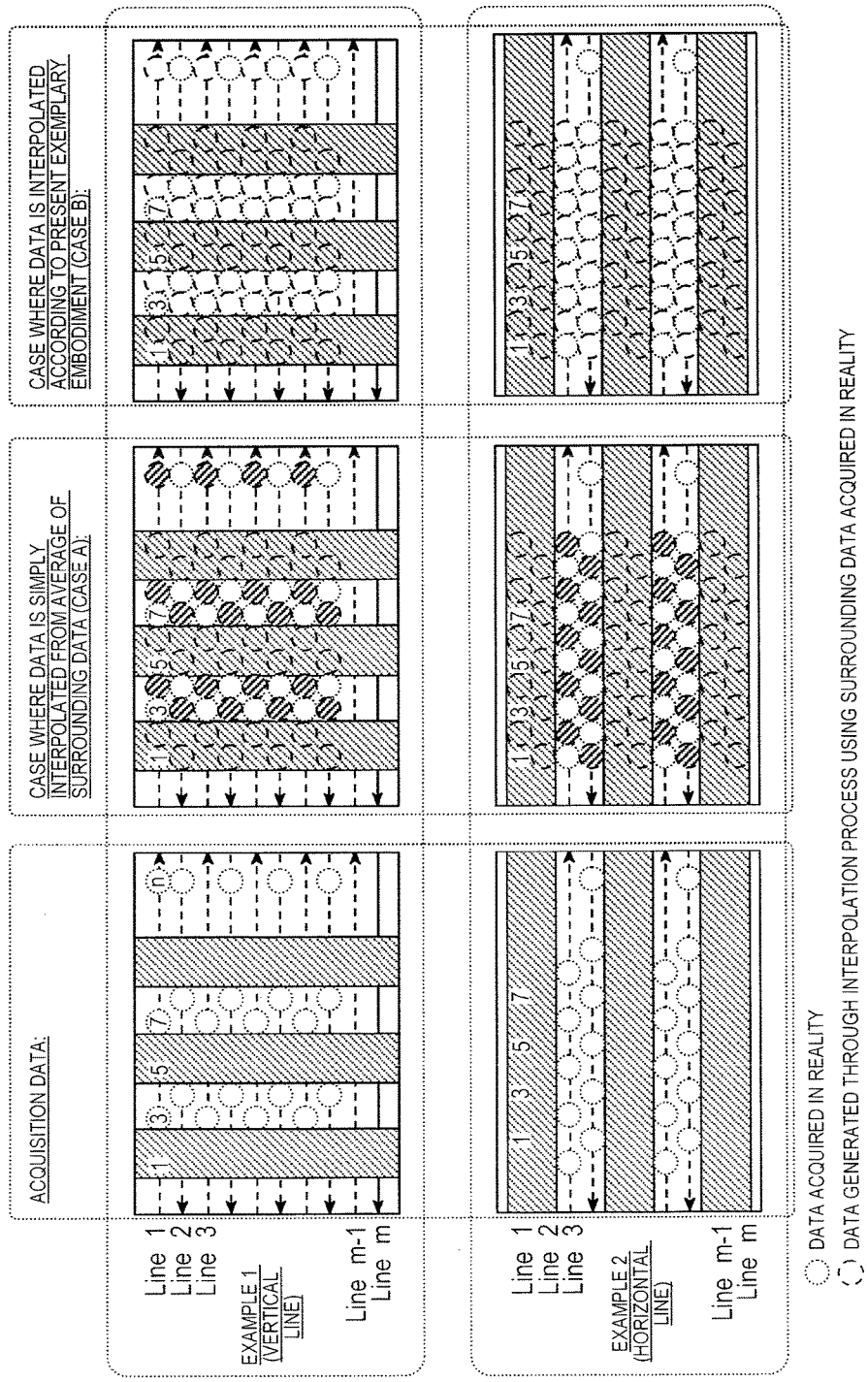
FIG. 10 is an explanatory diagram of an advantage of the interpolation process in the invisible light sensor according to the first exemplary embodiment.

Hereinafter, the details of the interpolation process in invisible light sensor NVSS according to the present exemplary embodiment will be described with reference to FIGS. 8 to 10. FIG. 8 is a schematic diagram showing an example of an operation outline of the interpolation process in invisible light sensor NVSS according to the first exemplary embodiment. FIG. 9 is a schematic diagram showing the type of the interpolation process on target area D5 of the interpolation process. FIG. 10 is an explanatory diagram of an advantage of the interpolation process in invisible light sensor NVSS according to the first exemplary embodiment.

In FIG. 8, invisible light sensor NVSS separates the reference-light acquisition data indicating the intensity of reflection light RV1 of each target area PT irradiated with reference light LS1 and the measuring-light acquisition data indicating the intensity of reflection light RV2 of each target area PT irradiated with measuring light LS2, and performs the above-described interpolation process on these data items, as described with reference to FIG. 7. The reference-light acquisition data is shown in the upper middle of FIG. 8, and the measuring-light acquisition data is shown in the lower middle of FIG. 8.

For example, invisible light sensor NVSS generates reference-light interpolation generation data in each target area PT (that is, each target area PT irradiated with measuring light LS2) which is not irradiated with reference light LS1 by performing the interpolation process using the reference-light acquisition data. The reference-light interpolation generation data is an estimation value of the reference-light acquisition data in a case where it is assumed that each target area PT (that is, each target area PT irradiated with measuring light LS2) which is not irradiated with reference light LS1 is irradiated with reference light LS1 calculated through the interpolation process using the reference-light acquisition data in surrounding target area PT.

For example, invisible light sensor NVSS generates the measuring-light interpolation generation data in each target area PT (that is, each target area PT irradiated with reference light LS1) which is not irradiated with measuring light LS2 by performing the interpolation process using the measuring-light acquisition data. The measuring-light interpolation generation data is an estimation value of the measuring-light acquisition data in a case where it is assumed that each target area PT (that is, each target area PT irradiated with reference light LS1) which is not irradiated with measuring light LS2 is irradiated with measuring light LS2 calculated through the interpolation process using the measuring-light acquisition data in surrounding target area PT.

FIG. 9 shows the type of the interpolation process depending on the number of target areas D1 to D4 present near target area D5 as a target of the interpolation process in detail. In the following description of FIGS. 9 and 10, the kinds of reference light LS1 and measuring light LS2 do not matter.

Specifically, target areas D3 and D4 are present therearound in a case where target area D5 is disposed on the upper left, target areas D2, D3, and D4 are present therearound in a case where target area D5 is disposed in the upper middle, target areas D2 and D4 are present therearound in a case where target area D5 is disposed on the upper right, target areas D1, D3, and D4 are present therearound in a case where target area D5 is disposed in the left middle, target areas D1, D2, D3, and D4 are present therearound in a case where target area D5 is disposed in the middle, target areas D1, D2, and D4 are present therearound in a case where target area D5 is disposed in the right middle, target areas D1 and D3 are present therearound in a case where target area D5 is disposed on the lower left, target areas D1, D2, and D3 are present therearound in a case where target area D5 is disposed in the lower middle, and target areas D1 and D2 are present therearound in a case where target area D5 is disposed on the lower right.

In a case where target area D5 is disposed on (in) the "upper left, upper middle, upper right, left middle, right middle, lower left, lower middle and lower right" except for "the middle", distance/substance detection processor 27a of detection processor 27 of invisible light sensor NVSS calculates, as the reference-light interpolation generation data or the measuring-light interpolation generation data in target area D5, an average value of reference-light acquisition data items or measuring-light acquisition data items in all the surrounding target areas adjacent to target area D5. That is, distance/substance detection processor 27a calculates the reference-light interpolation generation data or the measuring-light interpolation generation data in target area D5, as the interpolation process result. DD1, DD2, DD3, and DD4 are the reference-light acquisition data items or the measuring-light acquisition data items in target areas D1, D2, D3, and D4, and DD5 is the reference-light acquisition data or the measuring-light acquisition data in target area D5.

$$\text{target area } D5 \text{ is disposed on the upper left} \rightarrow DD5 = (DD3+DD4)/2 \tag{1}$$

$$\text{target area } D5 \text{ is disposed in the upper middle} \rightarrow DD5 = (DD2+DD3+DD4)/3 \tag{2}$$

$$\text{target area } D5 \text{ is disposed in the upper right} \rightarrow DD5 = (DD2+DD4)/2 \tag{3}$$

$$\text{target area } D5 \text{ is disposed in the left middle} \rightarrow DD5 = (DD3+DD1+DD4)/3 \tag{4}$$

$$\text{target area } D5 \text{ is disposed in the right middle} \rightarrow DD5 = (DD2+DD1+DD4)/3 \tag{5}$$

$$\text{target area } D5 \text{ is disposed in the lower left} \rightarrow DD5 = (DD3+DD1)/2 \tag{6}$$

$$\text{target area } D5 \text{ is disposed in the lower middle} \rightarrow DD5 = (DD2+DD3+DD1)/3 \tag{7}$$

$$\text{target area } D5 \text{ is disposed in the lower right} \rightarrow DD5 = (DD2+DD1)/2 \tag{8}$$

Accordingly, since invisible light sensor NVSS performs the interpolation process on the intensity value of reflection light RV1 or RV2 of reference light LS1 or measuring light LS2 in target area PT (specific target area) which is not irradiated with reference light LS1 or measuring light LS2 by using an average value of the intensity values of reflection light RV1 or RV2 of reference light LS1 or measuring light LS2 in a plurality of target areas PT adjacent to the specific target area, it is possible to suppress the erroneous detection of the specific substance by detecting the specific substance by using the interpolation process result.

Meanwhile, in a case where target area D5 is disposed in the "middle" and a great change is not present in the reference-light acquisition data or the measuring-light acquisition data in the vertical direction or the horizontal direction (specifically, absolute value of (DD1−DD4)≤k and absolute value of (DD2−DD3)≤l), distance/substance detection processor 27a calculates an average value of reference-light acquisition data items or measuring-light acquisition data items in four surrounding target areas D1, D2, D3, and D4, as the reference-light interpolation generation data or the measuring-light interpolation generation data in target area D5. Accordingly, DD5=(DD1+DD2+DD3+DD4)/4. k and l are integers.

For example, in a case where target area D5 is disposed in the "middle" and a great change is present in the horizontal direction, as a great change in the reference-light acquisition data or the measuring-light acquisition data in the vertical direction or the horizontal direction (specifically, absolute value of (DD1−DD4)<absolute value of (DD2−DD3), distance/substance detection processor 27a calculates an average value of the reference-light acquisition data items or the measuring-light acquisition data items in two adjacent target areas D1 and D4 having a small difference therebetween in the horizontal direction, as the reference-light interpolation generation data or the measuring-light interpolation generation data in target area D5. Accordingly, DD5=(DD1+DD4)/2.

For example, in a case where target area D5 is disposed in the "middle" and a great change is present in the vertical direction, as a great change in the reference-light acquisition data or the measuring-light acquisition data in the vertical direction or the horizontal direction (specifically, absolute value of (DD1−DD4)≥absolute value of (DD2−DD3)), distance/substance detection processor 27a calculates an average value of the reference-light acquisition data items or the measuring-light acquisition data items in two adjacent target areas D2 and D3 having a small difference therebetween in the vertical direction, as the reference-light interpolation generation data or the measuring-light interpolation generation data in target area D5. Accordingly. DD5=(DD2+DD3)/2.

For example, the upper and lower figures on the leftmost of FIG. 10 depict the advantages of the method of calculating the reference-light interpolation generation data or the measuring-light interpolation generation data in target area D5 in a case where target area D5 is disposed in the "middle" in FIG. 9, and depict the reference-light acquisition data or the measuring-light acquisition data (simply referred to as "acquisition data" in the description of FIG. 10) in a case where strength and weakness of reflection light RV1 or reflection light RV2 appear in the vertical direction (see Example 1) or the horizontal direction (see Example 2) of detection area K.

The upper and lower figures in the middle of FIG. 10 depict an example in which since target area D5 is disposed in the "middle" and a great change is caused in the reference-light acquisition data or the measuring-light acquisition data in the vertical direction or the horizontal direction in FIG. 9, such a change is compensated by distance/substance detection processor 27a, and depict an example in a case where an average value of the reference-light acquisition data items or the measuring-light acquisition data items in four surrounding target areas D1, D2, D3, and D4 is calculated as the reference-light interpolation generation data or the measuring-light interpolation generation data in target area D5 (see Case A).

The upper and lower figures on the rightmost of FIG. 10 depict an example in which since target area D5 is disposed in the "middle" and a great change is caused in the reference-light acquisition data or the measuring-light acquisition data in the vertical direction or the horizontal direction in FIG. 9, such a change is compensated by distance/substance detection processor 27a, and depict an example in which an average value of the reference-light acquisition data items or the measuring-light acquisition data items in two adjacent target areas (D2 and D3) or (D1 and D4) having a small difference in the vertical direction is calculated as the reference-light interpolation generation data or the measuring-light interpolation generation data in target area D5 (see Case B).

For example, in order to easily understand the description of FIG. 10, acquisition data in a black area is "0", and acquisition data in a white area is "100".

In Case A shown in FIG. 10, distance/substance detection processor 27a acquires "25" as the calculation result of an average value of acquisition data items of four target areas (specifically, the number of target areas as the black area is 3 and the number of target areas as the white area is 1) near target area D5 as the black area which is the target of the interpolation process, as the reference-light interpolation generation data or the measuring-light interpolation generation data in the black area, in both Example 1 and Example 2 of this drawing. Similarly, distance/substance detection processor 27a acquires "75" as the calculation result of an average value of acquisition data items of four target areas (specifically, the number of target areas as the black area is 1 and the number of target areas as the white area is 3) near target area D5 as the white area which is the target of the interpolation process, as the reference-light interpolation generation data or the measuring-light interpolation generation data in the white area.

Accordingly, in Case A, since the reference-light interpolation generation data or the measuring-light interpolation generation data is "25" or "75" and has a great error from the acquisition data having a value of "0" in the black area or the acquisition data having a value of "100" in the white area, the accuracy of the interpolation process is deteriorated.

Meanwhile, in Case B shown FIG. 10, distance/substance detection processor 27a acquires "0" as the calculation result of an average value of acquisition data items in two adjacent target areas having a small difference in the horizontal direction or the vertical direction, among four target areas (specifically, the number of target areas as the black area is 3 and the number of target areas as the white area is 1) near target area D5 as the black area which is the target of the interpolation process, as the reference-light interpolation generation data and the measuring-light interpolation generation data in the black area in both Example 1 and Example 2 of this drawing. Similarly, distance/substance detection processor 27a acquires "100" as the calculation result of an average value of acquisition data items in two adjacent target areas having a small difference in the horizontal direction or the vertical direction, among four target areas (specifically, the number of target areas as the black area is 1 and the number of target areas as the white area is 3) near target area D5 as the white area which is the interpolation process, as the reference-light interpolation generation data or the measuring-light interpolation generation data in the white area.

Accordingly, in Case B, since the reference-light interpolation generation data or the measuring-light interpolation generation data is "0" or "100" and matches to the acquisition data having a value of "0" in the black area or the acquisition data having a value of "100" in the white area, distance/substance detection processor 27a uses an average value of acquisition data items in two adjacent target areas having a small difference in the horizontal direction or the vertical direction, as the interpolation process in a case where target area D5 is disposed in the "middle" as shown in FIG. 9, and thus, it is possible to suppress a deterioration in the accuracy of the interpolation process. In other words, since the interpolation process result complying with the intensity value of reflection light RV1 or RV2 of reference light LS1 or measuring light LS2 in the horizontal direction or the vertical direction of a specific target area is acquired, invisible light sensor NVSS can further improve interpolation accuracy than that in a case where the invisible light sensor simply uses the average value of the intensity values of reflection light RV1 or RV2 of reference light LS1 or measuring light LS2 in target areas PT near target area D5

(specific target area). Thus, the specific substance is detected using the interpolation process result, and it is possible to suppress the erroneous detection of the specific substance.
(Detection Process of Specific Substance in Invisible Light Sensor)

Hereinafter, the detection process of the specific substance in invisible light sensor NVSS according to the present exemplary embodiment will be described with reference to FIGS. 11A and 11B. FIG. 11A is an explanatory diagram showing an example of timings of the projection of first projection light source 13 and second projection light source 15 and the detection process of the measuring target substance according to a comparative example. FIG. 11B is an explanatory diagram showing an example of timings of the projection of first projection light source 13 and second projection light source 15 and the detection process of the measuring target substance according to the first exemplary embodiment.

In the comparative example shown in FIG. 11A, reference-light acquisition data is acquired as input data in an odd-numbered frame, and measuring-light acquisition data is acquired as input data in an even-numbered frame. As intermediate data for detecting whether or not the specific substance is present in detection area K, invisible light sensor NVSS uses the reference-light acquisition data acquired in the odd-numbered frame and the measuring-light acquisition data acquired in the even-numbered frame directly before this odd-numbered frame in the odd-numbered frames, and uses the measuring-light acquisition data acquired in the even-numbered frame and the reference-light acquisition data acquired in the odd-numbered frame directly before this even-numbered frame in the even-numbered frames. Accordingly, in FIG. 11A, as much of input data items as at least two frames are necessary in order to detect the specific substance.

Meanwhile, in the present exemplary embodiment shown in FIG. 11B, since the interpolation process using the reference-light acquisition data or the measuring-light acquisition data is performed in one frame irrespective of the odd-numbered or even-numbered frames, a pair of reference-light acquisition data and reference-light interpolation generation data and a pair of measuring-light acquisition data and measuring-light interpolation generation data are acquired as input data and intermediate data in one frame, and thus, invisible light sensor NVSS can detect the specific substance in one frame.
(Projection Patterns of Reference Light and Measuring Light in Invisible Light Sensor)

Hereinafter, the projection patterns of reference light LS1 and measuring light LS2 in invisible light sensor NVSS according to the present exemplary embodiment will be described with reference to FIGS. 12A, 12B, 12C, 13A, 13B, 13C, 14A, 14B, and 14C.

Figures 12A, 12B, 12C:
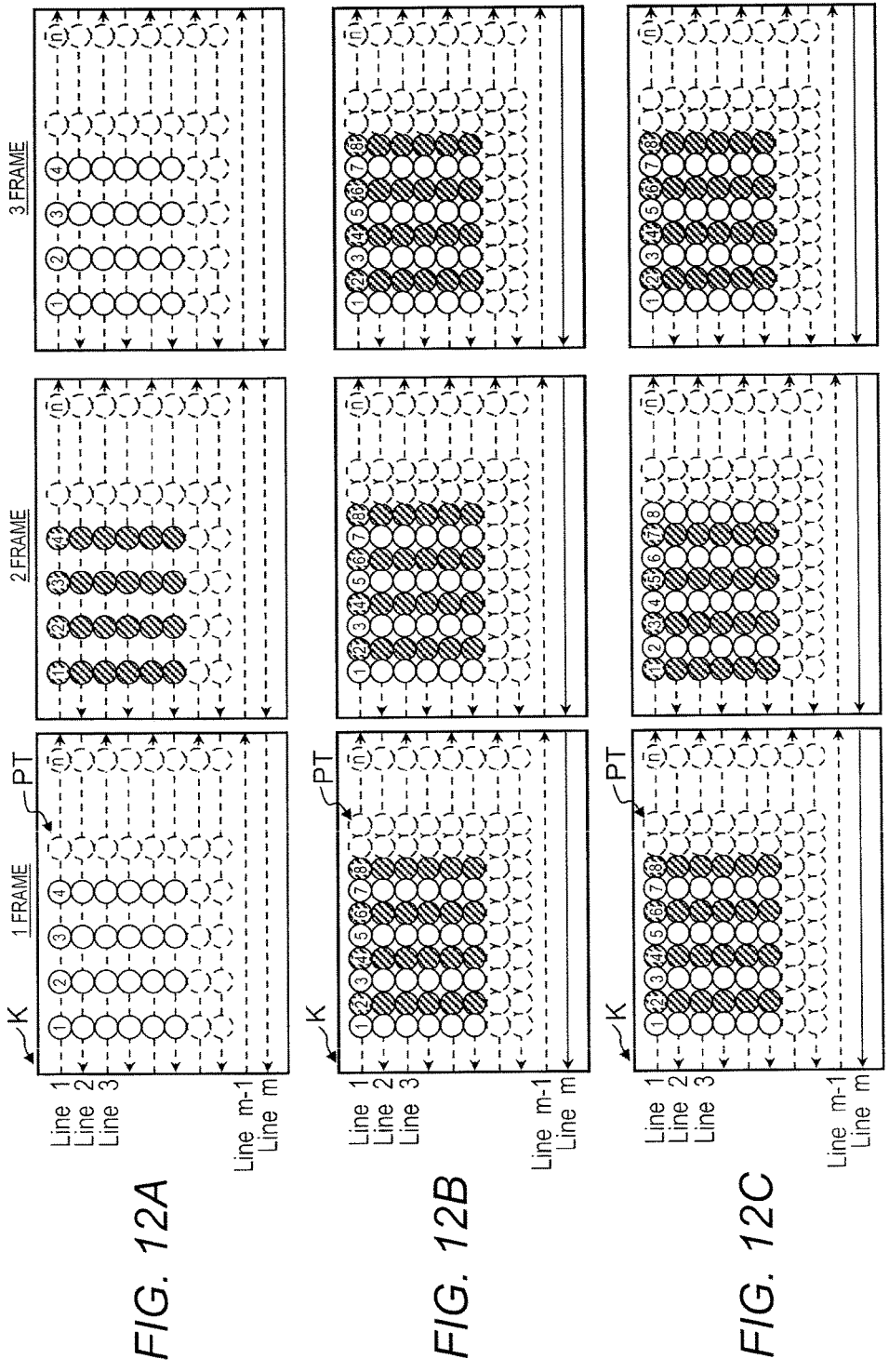
FIG. 12A is an explanatory diagram showing an example of a first projection pattern formed by the first projection light source and the second projection light source according to a comparative example.
FIG. 12B is an explanatory diagram showing an example of a second projection pattern formed by the first projection light source and the second projection light source according to the first exemplary embodiment.
FIG. 12C is an explanatory diagram showing an example of a third projection pattern formed by the first projection light source and the second projection light source according to the first exemplary embodiment.

FIG. 12A is an explanatory diagram showing an example of a first projection pattern formed by first projection light source 13 and second projection light source 15 according to a comparative example. FIG. 12B is an explanatory diagram showing an example of a second projection pattern formed by first projection light source 13 and second projection light source 15 according to the first exemplary embodiment. FIG. 12C is an explanatory diagram showing an example of a third projection pattern formed by first projection light source 13 and second projection light source 15 according to the first exemplary embodiment.

Figures 13A, 13B, 13C:
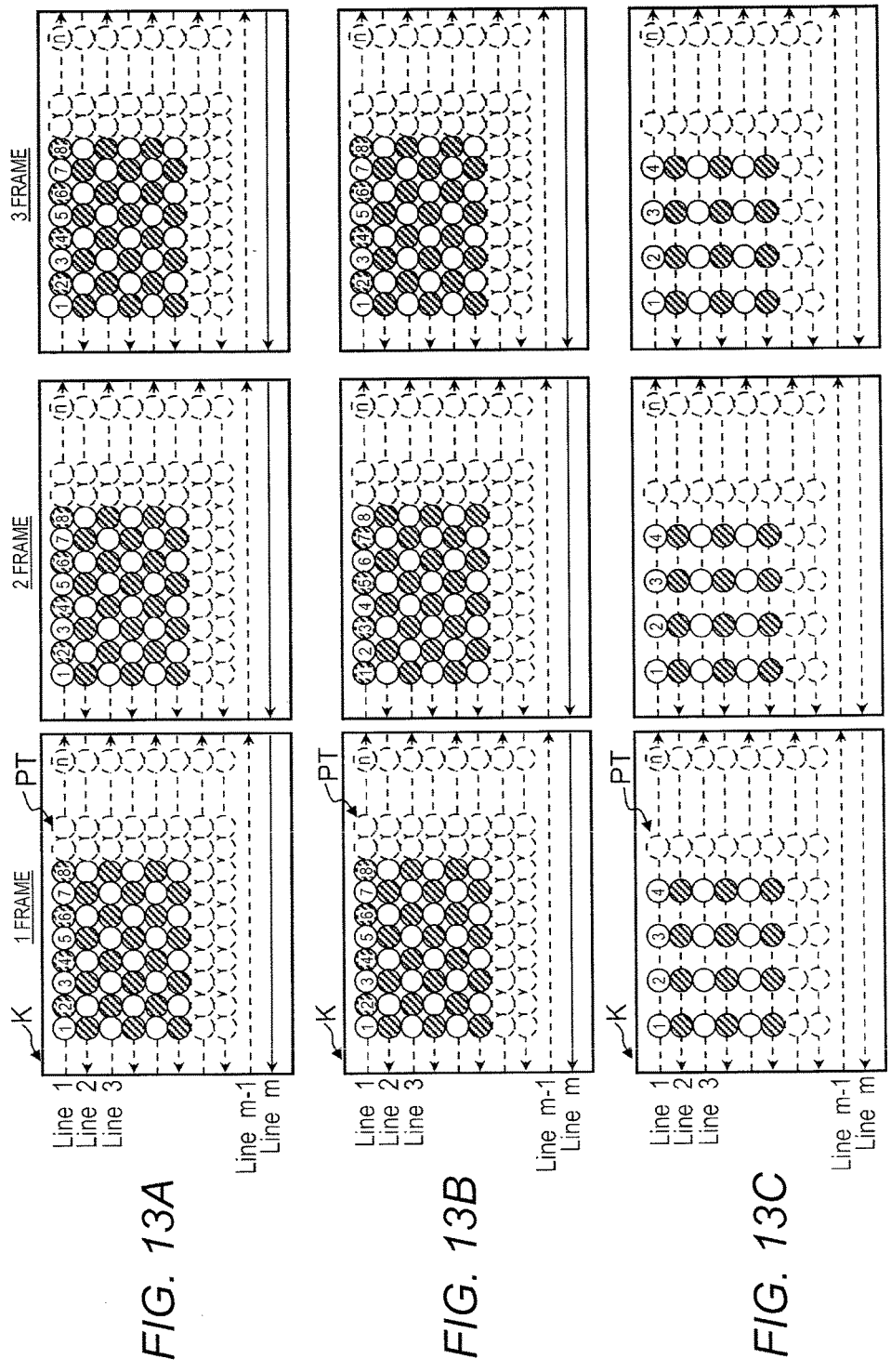
FIG. 13A is an explanatory diagram showing an example of a fourth projection pattern formed by the first projection light source and the second projection light source according to the first exemplary embodiment.
FIG. 13B is an explanatory diagram showing an example of a fifth projection pattern formed by the first projection light source and the second projection light source according to the first exemplary embodiment.
FIG. 13C is an explanatory diagram showing an example of a sixth projection pattern formed by the first projection light source and the second projection light source according to the first exemplary embodiment.

FIG. 13A is an explanatory diagram showing an example of a fourth projection pattern formed by first projection light source 13 and second projection light source 15 according to the first exemplary embodiment. FIG. 13B is an explanatory diagram showing an example of a fifth projection pattern formed by first projection light source 13 and second projection light source 15 according to the first exemplary embodiment. FIG. 13C is an explanatory diagram showing an example of a sixth projection pattern formed by first projection light source 13 and second projection light source 15 according to the first exemplary embodiment.

Figures 14A, 14B, 14C:
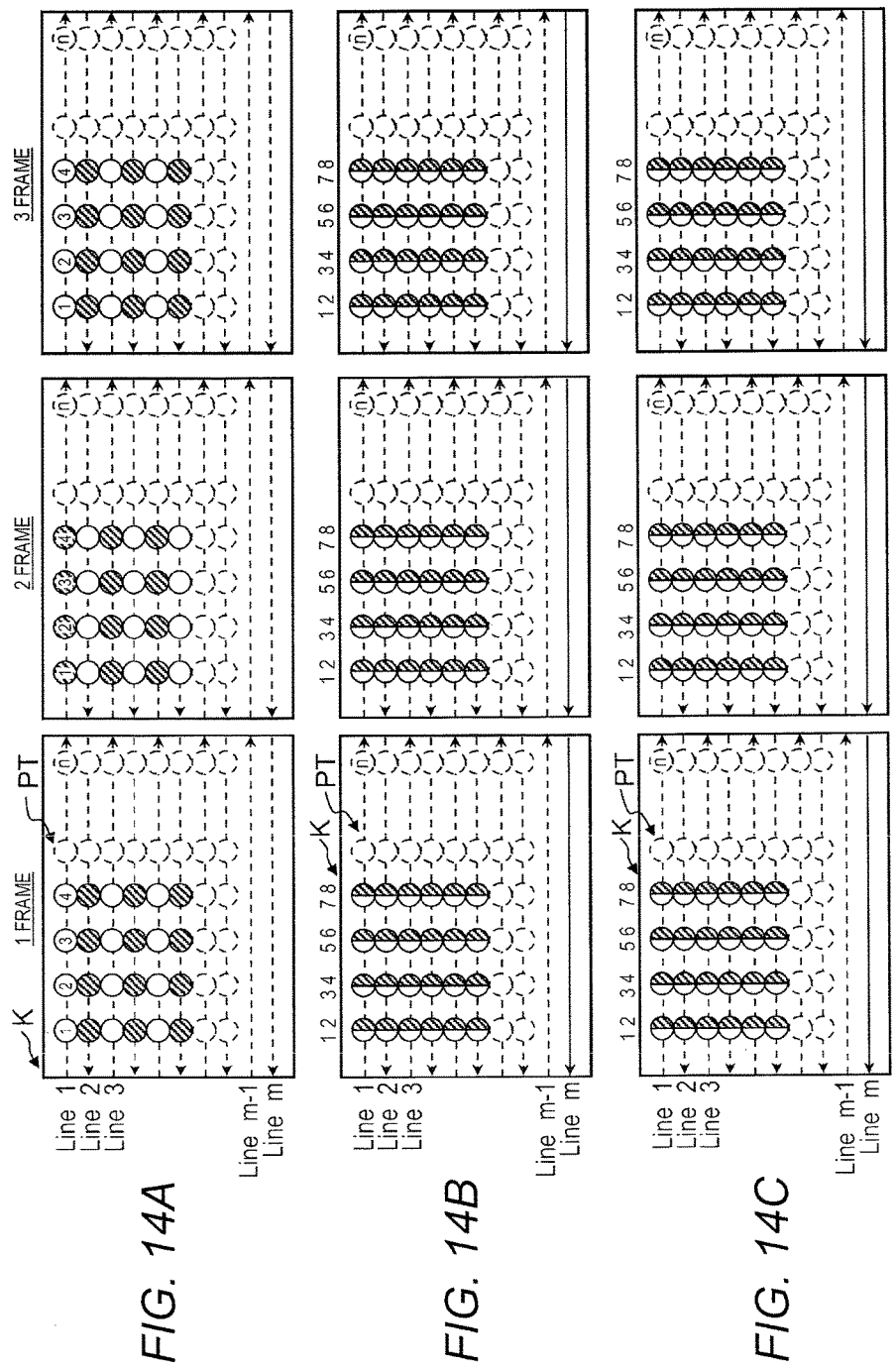
FIG. 14A is an explanatory diagram showing an example of a seventh projection pattern formed by the first projection light source and the second projection light source according to the first exemplary embodiment.
FIG. 14B is an explanatory diagram showing an example of an eighth projection pattern formed by the first projection light source and the second projection light source according to the first exemplary embodiment.
FIG. 14C is an explanatory diagram showing an example of a ninth projection pattern formed by the first projection light source and the second projection light source according to the first exemplary embodiment.

FIG. 14A is an explanatory diagram showing an example of a seventh projection pattern formed by first projection light source 13 and second projection light source 15 according to the first exemplary embodiment. FIG. 14B is an explanatory diagram showing an example of an eighth projection pattern formed by first projection light source 13 and second projection light source 15 according to the first exemplary embodiment. FIG. 14C is an explanatory diagram showing an example of a ninth projection pattern formed by first projection light source 13 and second projection light source 15 according to the first exemplary embodiment.

In the first projection pattern according to the comparative example shown in FIG. 12A, invisible light sensor NVSS discretely applies reference light LS1 to each target area PT of detection area K in the horizontal direction from first projection light source 13 in the odd-numbered frame, and discretely applies measuring light LS2 to each target area PT of detection area K in the horizontal direction from second projection light source 15 in the even-numbered frames.

In the second projection pattern according to the present exemplary embodiment shown in FIG. 12B, invisible light sensor NVSS alternately switches between reference light LS1 and measuring light LS2 to irradiate each target area PT adjacent in the horizontal direction of an initial line (Line 1) of detection area K and alternately switches between reference light LS1 and measuring light LS2 to irradiate each target area PT adjacent in the horizontal direction in the next line (Line 2) in the same manner, for every frame. Accordingly, since invisible light sensor NVSS alternately switches between reference light LS1 and measuring light LS2 so as to be adjacent to each other to irradiate each target area PT adjacent in the horizontal direction, which correspond to a single pixel constituting the visible light image data of detection area K, it is possible to reduce a time difference between the projection timing of reference light LS1 and the projection timing of measuring light LS2, and thus, it is possible to detect whether or not the specific substance is present in target area PT of detection area K in the horizontal direction with high accuracy based on reflection light beams RV1 and RV2 of reference light LS1 and measuring light LS2 of adjacent pixels in the horizontal direction. Since invisible light sensor NVSS alternately switches between reference light LS1 and measuring light LS2 to irradiate each vertical direction of detection area K from first projection light source 13 and second projection light source 15, it is possible to easily control the projection timings of reference light LS1 and measuring light LS2.

Unlike the second projection pattern, in the third projection pattern according to the present exemplary embodiment shown in FIG. 12C, since invisible light sensor NVSS switches the application order of reference light LS1 and measuring light LS2 for each frame indicating the surface irradiation of the entire detection area K, reflection light beams RV1 and RV2 of reference light LS1 and measuring light LS2 to target areas PT of detection area K are compared between the frames (for example, the first frame and the second frame, and the same applies hereinafter), and thus, the acquisition data items of reflection light beams RV1 and RV2 of reference light LS1 and measuring light LS2 in the same target area PT are acquired. Thus, it is possible to detect the specific substance in the horizontal direction of detection area K with higher accuracy than that in a case where the reference light LS1 and measuring light LS2 are not projected in the same target area PT in addition to the advantage of the second projection pattern. For example, in the third projection pattern, in a case where a column is present in a line (for example, in the leftmost line of the odd-numbered frame of FIG. 12C) of detection area K in the vertical direction, invisible light sensor NVSS is not able to sufficiently detect that the column is present in the interpolation process result in the second projection pattern in some cases, but is able to use the intensity of reflection light RV2 of measuring light LS2 in the third projection pattern. Thus, it is possible to precisely detect that the column is normally present.

Unlike the second projection pattern, in the fourth projection pattern according to the present exemplary embodiment shown in FIG. 13A, since invisible light sensor NVSS alternately switches between reference light LS1 and measuring light LS2 to irradiate each target area PT adjacent in the vertical direction of detection area K from first projection light source 13 and second projection light source 15, it is possible to improve the detection accuracy of the specific substance in both the horizontal direction and the vertical direction of detection area K in addition to the advantage of the second projection pattern.

Unlike the fourth projection pattern, in the fifth projection pattern according to the present exemplary embodiment shown in FIG. 13B, since invisible light sensor NVSS switches the application order of reference light LS1 and measuring light LS2 for each target area PT adjacent both in the vertical direction and the horizontal direction of detection area K for each frame indicating the surface irradiation of the entire detection area K, reflection light beams RV1 and RV2 of reference light LS1 and measuring light LS2 to target areas PT of detection area K are compared between the frames, and thus, the acquisition data items of reflection light beams RV1 and RV2 of reference light LS1 and measuring light LS2 in the same target area PT acquired. Thus, it is possible to detect the specific substance in both the horizontal direction and the vertical direction of detection area K with higher accuracy than that in a case where the reference light LS1 and measuring light LS2 are not projected in the same target area PT in addition to the advantage of the fourth projection pattern.

In the sixth projection pattern according to the present exemplary embodiment shown in FIG. 13C, invisible light sensor NVSS controls the application timings of reference light LS1 and measuring light LS2 to detection area K for each target area PT corresponding to a single pixel in a time-division manner, uniformly applies reference light LS1 or measuring light LS2 in the horizontal direction of detection area K, and alternately switches between reference light LS1 and measuring light LS2 to irradiate each target area PT adjacent in the vertical direction of detection area K. Accordingly, for example, even in a case where it is difficult to apply reference light LS1 and measuring light LS2 to each target area PT adjacent in the horizontal direction of detection area K, invisible light sensor NVSS applies only reference light LS1 or applies only measuring light LS2 to each horizontal direction of detection area K, and thus, it is possible to easily control the projection timings of reference light LS1 and measuring light LS2.

Unlike the sixth projection pattern, in the seventh projection pattern according to the present exemplary embodiment shown in FIG. 14A, since invisible light sensor NVSS switches the application order of reference light LS1 and measuring light LS2 for each frame indicating the surface irradiation of the entire detection area K, reflection light beams RV1 and RV2 of reference light LS1 and measuring light LS2 to target areas PT which are not adjacent in the horizontal direction of detection area K and are adjacent in the vertical direction are compared between the frames, and thus, the acquisition data items of reflection light beams RV1 and RV2 of reference light LS1 and measuring light LS2 in the same target area PT are acquired. Thus, it is possible to detect the specific substance in the horizontal direction of detection area K with higher accuracy than that in a case where the reference light LS1 and measuring light LS2 are not projected in the same target area PT.

Here, a method of the eighth projection pattern and the ninth projection pattern of reference light LS1 and measuring light LS2 in invisible light sensor NVSS according to the present exemplary embodiment will be described.

Figure 15:
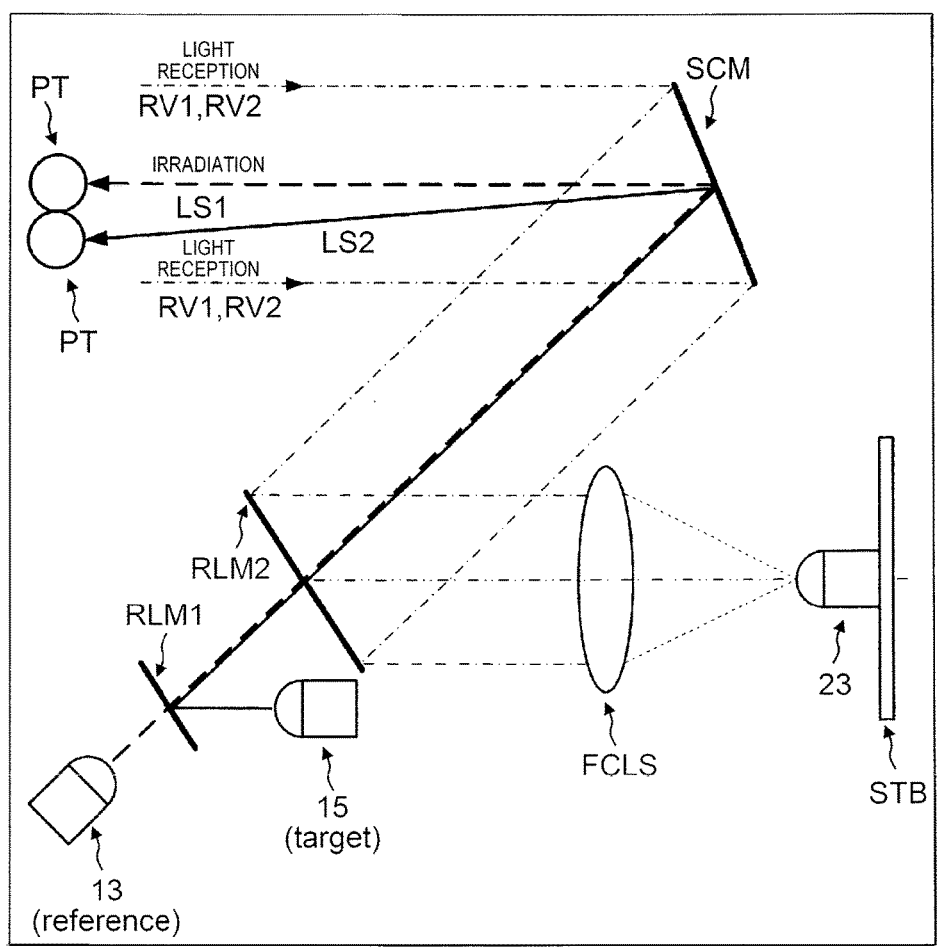
FIG. 15 is a block diagram showing a second configuration example of the projection light scanner and the image pick up related to reception of the reflection light and the projection of the reference light and the measuring light of the invisible light sensor according to the first exemplary embodiment.

FIG. 15 is a block diagram showing a second configuration example of the projection light scanner and the image pick up related to the reflection light and the projection of the reference light and the measuring light of the invisible light sensor in the first exemplary embodiment. The second configuration example of projection light scanner 17 and image pick shown in FIG. 15 are used for the eighth projection pattern and the ninth projection pattern to be described below. In the description of FIG. 15, the description of the same content as that in the description of FIG. 4 will be omitted, and different contents will be described.

Figure 17A:
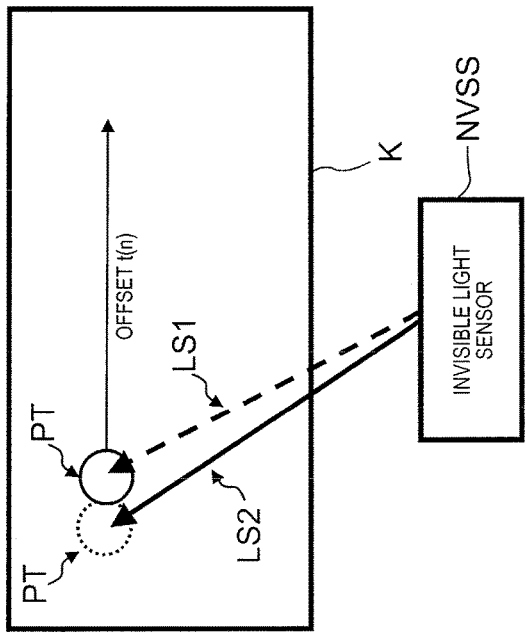
FIG. 17A is an explanatory diagram showing an example of images of projection positions of projection light beams (measuring light and reference light) in the second projection pattern to the seventh projection pattern.
Figure 17B:
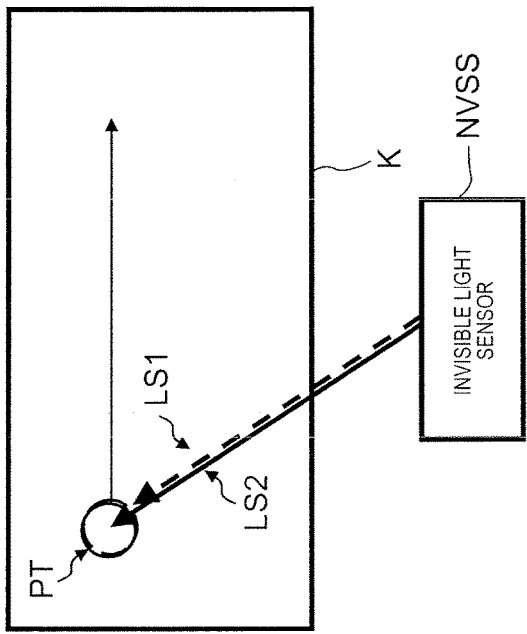
FIG. 17B is an explanatory diagram showing an example of images of projection positions of the projection light beams (measuring light and reference light) in the eighth projection pattern and the ninth projection pattern.
Figure 17C:
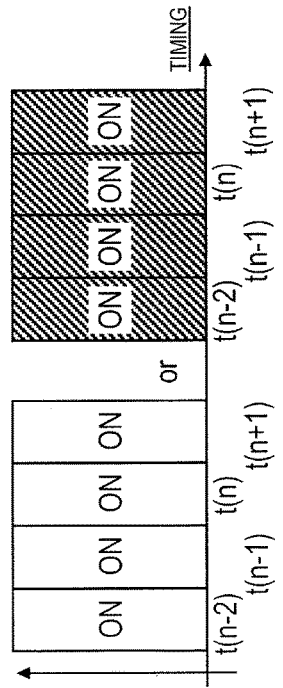
FIG. 17C is an explanatory diagram showing an example of the projection timings of the first projection light source and the second projection light source in the second projection pattern to the fifth projection pattern, the eighth projection pattern, and the ninth projection pattern.
Figure 17D:
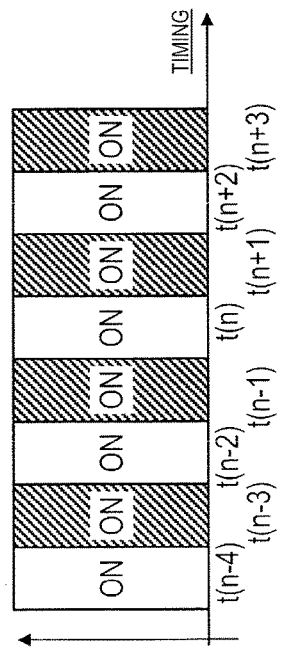
FIG. 17D is an explanatory diagram showing an example of the projection timings of the first projection light source and the second projection light source in the sixth projection pattern and the seventh projection pattern.

FIGS. 16A to 16D are explanatory diagrams showing examples of images of projection positions of first projection light source 13 and second projection light source 15 in the eighth projection pattern and the ninth projection pattern in a sequence of time. FIG. 17A is an explanatory diagram showing images of projection positions of projection light beams (measuring light LS2 and reference light LS1) of the second projection pattern to the seventh projection pattern. FIG. 17B is an explanatory diagram showing images of projection positions of projection light beams (measuring light LS2 and reference light LS1) of the eighth projection pattern and the ninth projection pattern. FIG. 17C is an explanatory diagram showing an example of the projection timings of first projection light source 13 and second projection light source 15 in the second projection pattern to the fifth projection pattern and the eighth projection pattern and the ninth projection pattern. FIG. 17D is an explanatory diagram showing an example of the projection timings of first projection light source 13 and second projection light source 15 in the sixth projection pattern and the seventh projection pattern.

Unlike FIG. 4, in FIG. 15, incidence angles are different from those of reference light LS1 and measuring light LS2 incident on scanning mirror SCM. Thus, a temporal offset equivalent to a difference $\{t(n+1)-t(n)\}$ is performed through scanning control performed by the stepping motor (not shown) such that scanning mirror SCM is able to irradiate two adjacent target areas PT of detection area K with only reference light LS1 at certain timing t(n) and is able to project only measuring light LS2 at the next timing t(n+1).

More specifically, at timing t(n) shown in FIG. 16A, the third target area PT from the left of the second line (Line 2) of detection area K is irradiated with only reference light LS1. Although the scanning control of scanning mirror SCM is performed at timing t(n) such that the second target area PT is irradiated with measuring light LS2 from the left of the same line (Line 2), measuring light LS2 is not output from second projection light source 15, and consequently, measuring light LS 2 is not applied.

At the next timing t(n+1) shown in FIG. 16B, scanning mirror SCM is moved from a position at timing t(n) through the scanning control of the stepping motor. Thus, since target area PT irradiated with reference light LS1 and measuring light LS2 is shifted by one in the horizontal direction, the third target area PT from the left of the second line (Line 2) of detection area K is irradiated with only measuring light LS2. Although the scanning control of scanning mirror SCM is performed at timing t(n+1) such that the fourth target area PT from the left of the same line (Line 2) is irradiated with reference light LS1, reference light LS1 is not output from first projection light source 13, and consequently, reference light LS1 is not applied.

Although the position of scanning mirror SCM is not changed from the position at timing t(n+1) at the next timing t(n+2) shown in FIG. 16C, since reference light LS1 is output from first projection light source 13 and measuring light LS2 is not output from second projection light source 15, the fourth target area PT from the left of the second line (Line 2) of detection area K is irradiated with only reference light LS1.

At the next timing t(n+3) shown in FIG. 16D, scanning mirror SCM is moved from the position at timing t(n+2) through the scanning control of the stepping motor. Thus, since target area PT irradiated with reference light LS1 and measuring light LS2 is shifted by one in the horizontal direction, the fourth target area PT from the left of the second line (Line 2) of detection area K is irradiated with only measuring light LS2. Although the scanning control of scanning mirror SCM is performed at timing t(n+3) such that the fifth target area PT from the left of the same line (Line 2) is irradiated with reference light LS1, reference light LS1 is not output from first projection light source 13, and consequently, reference light LS1 is not applied.

As stated above, in the eighth projection pattern and the ninth projection pattern, invisible light sensor NVSS can irradiate the same target area PT of detection area K with both reference light LS1 and measuring light LS2 in a state in which a timing difference {t(n+i)−t(n+(i−1))} (i: an integer which is equal to or greater than 2) of equivalent to as much as a half-pixel is delayed. In the eighth projection pattern, reference light LS1 is applied earlier, and measuring light LS2 is delayed as much as the half-pixel and is applied later (see FIG. 14B). In the ninth projection pattern, scanning control in which a scanning direction is inverted for each line is performed, and is performed such that reference light LS1 is applied earlier and measuring light LS2 is delayed as much as the half-pixel and is applied later in the odd-numbered (for example, the first, the third, the fifth, . . . , and the same applies hereinafter.) lines, and measuring light LS2 is applied earlier and reference light LS1 is delayed as much as the half-pixel and is applied later in the even-numbered (for example, the second, the fourth, the sixth, . . . , and the same applies hereinafter.) lines (see FIG. 14C). In the eighth projection pattern and the ninth projection pattern, an offset amount (that is, a difference in time when reference light LS1 or measuring light LS2 is delayed and applied) is not limited to the time difference corresponding to the half-pixel, and may be, for example, a time difference corresponding to one pixel or two pixels. Accordingly, since invisible light sensor NVSS is able to irradiate the same target area PT with reference light LS1 and measuring light LS2 with a slight time difference (see the above-described timing difference {t(n+i) t(n+(i−1))}), it is possible to further reduce a time difference for irradiating the same target area PT with reference light LS1 and measuring light LS2 than that in a case where the entire detection area K is irradiated with only measuring light LS2 after the entire detection area K is irradiated with only reference light LS1, and it is possible to detect the specific substance in detection area K with high accuracy.

In the second projection pattern to the seventh projection pattern shown in FIG. 17A, since the incidence angles of reference light LS1 and measuring light LS2 on scanning mirror SCM are the same, if reference light LS1 and measuring light LS2 are output from first projection light source 13 and second projection light source 15 at the same timing (for example, timing t(n)), invisible light sensor NVSS can irradiate the same target area PT.

Meanwhile, in the eighth projection pattern and the ninth projection pattern shown in FIG. 17B, since the incidence angles of reference light LS1 and measuring light LS2 on scanning mirror SCM are different, reference light LS1 and measuring light LS2 are not output from first projection light source 13 and second projection light source 15 at the same timing (for example, timing t(n)) and any one light beam is output earlier and the other one light beam is output at the next timing (for example, timing t(n+1)), and thus, invisible light sensor NVSS can irradiate the same target area PT with reference light LS1 and measuring light LS2 not at the same timing but at two continuous output timings.

In the second projection pattern to the fifth projection pattern, and the eighth projection pattern and the ninth projection pattern shown in FIG. 17C, invisible light sensor NVSS alternately projects (outputs) reference light LS1 or measuring light LS2 from first projection light source 13 or second projection light source 15 at each projection timing (that is, each timing when timing signal TR for light scanning is output to first projection light source 13 or second projection light source 15).

Meanwhile, in the sixth projection pattern and the seventh projection pattern shown in FIG. 17D, invisible light sensor NVSS evenly projects (outputs) only reference light LS1 or only measuring light LS2 from first projection light source 13 or second projection light source 15 onto each target area PT of the line of detection area K in the horizontal direction without limiting to a projection timing (that is, timing when timing signal TR for light scanning is output to first projection light source 13 or second projection light source 15).

(Description of Detailed Operation of Substance Detection of Invisible Light Sensor)

Figure 22:
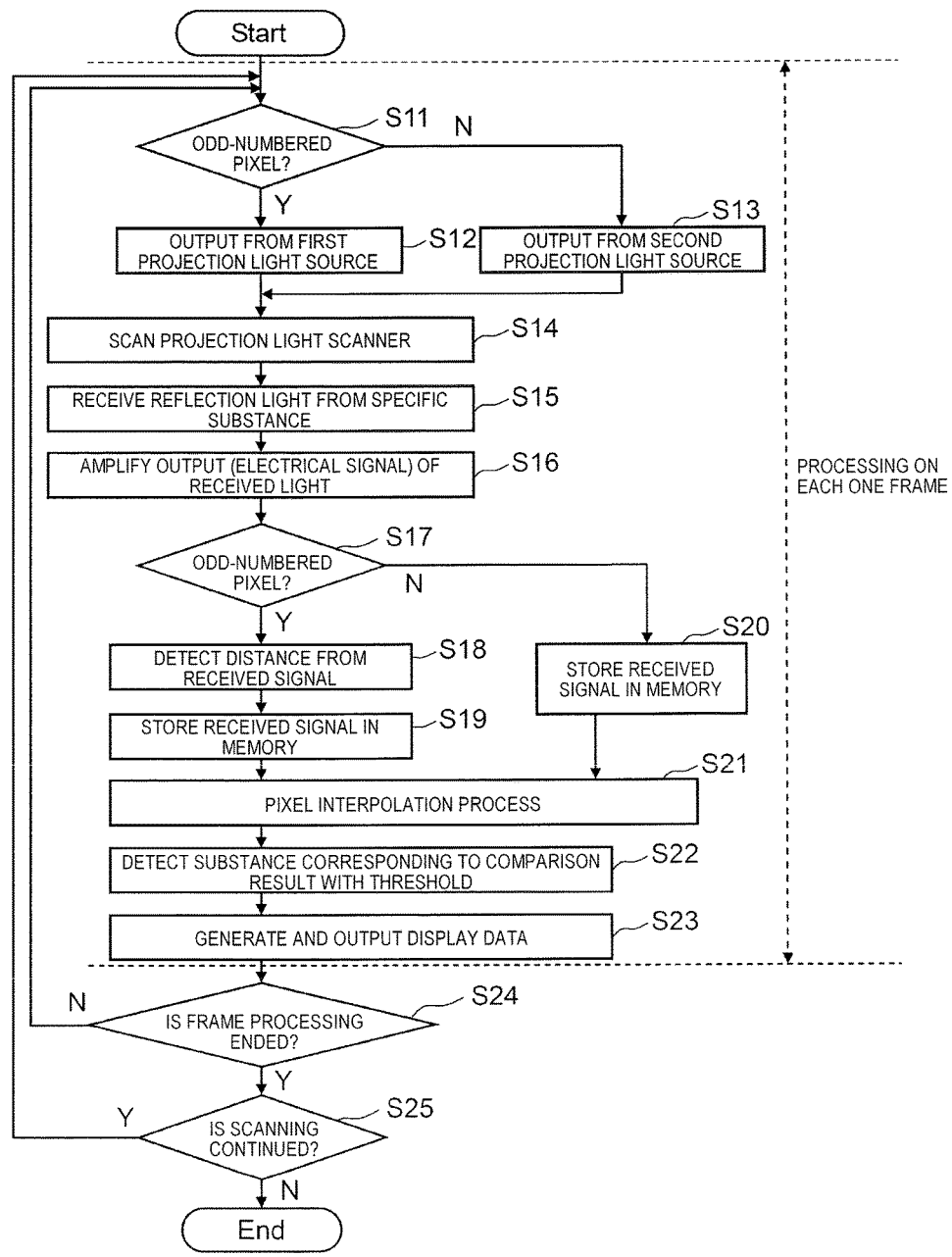
FIG. 22 is a flowchart for describing an example of the detailed operation procedure of the substance detection in the invisible light sensor according to the first exemplary embodiment.

Hereinafter, the detailed operation procedure of the substance detection in invisible light sensor NVSS according to the present exemplary embodiment will be described with reference to FIG. 22. FIG. 22 is a flowchart for describing an example of the detailed operation procedure of the substance detection in invisible light sensor NVSS according to the first exemplary embodiment.

In FIG. 22, timing controller 11*a* outputs timing signal TR for light scanning to any one or both of first projection light source 13 and second projection light source 15 when the corresponding target area PT of detection area K is irradiated with any one or both of reference light LS1 and measuring light LS2.

Thus, in a case where odd-numbered target area PT (corresponding to the odd-numbered pixel) of any one line of detection area K in the horizontal direction is irradiated (S11, Y), timing controller 11*a* outputs timing signal TR for light scanning to first projection light source 13. First projection light source 13 outputs reference light LS1 having the first wavelength (for example, 1.1 μm) in response to input of light output signal RF from timing controller 11*a* (S12).

Meanwhile, in a case where even-numbered target area PT (corresponding to the even-numbered pixel) of any one line of detection area K in the horizontal direction is irradiated (S11, N), timing controller 11*a* outputs timing signal TR for light scanning to second projection light source 15. Second projection light source 15 outputs measuring light LS2 having a second wavelength (for example, 1.45 μm) in response to input of light output signal RF from timing controller 11*a* (S13).

Projection light scanner 17 scans such that the corresponding odd-numbered or even-numbered target area PT of detection area K is able to be irradiated with reference light LS1 or measuring light LS2 (S14). In a case where the specific substance is present in the corresponding odd-numbered or even-numbered target area PT of detection area K, reflection light RV1 or reflection light RV2 which are reflection light of reference light LS1 or measuring light LS2 from the specific substance is received by light receiver 23 through image pick up 21 (S15).

In signal processor 25, the output (electrical signal) of reflection light RV1 in light receiver 23 is converted into the voltage signal, and a level of the voltage signal is amplified to a level capable of being processed in comparator/peak hold processor 25*c* (S16). Comparator/peak hold processor 25*c* binarizes the output signal of amplifier 25*b*, and outputs the binarized signal to distance/substance detection processor 27*a* depending on the comparison result of the output signal of amplifier 25*b* with a predetermined threshold. Comparator/peak hold processor 25*c* outputs information of the output signal of amplifier 25*b* to distance/substance detection processor 27*a*.

In a case where information of the odd-numbered pixel (odd-numbered target area PT) in any one line of detection area K in the horizontal direction is acquired in step S16 (S17, Y), distance/substance detection processor 27*a* measures the distance between invisible light sensor NVSS and the specific substance based on the output (binarized signal) of reflection light RV1 of reference light LS1 having the first wavelength (for example, 1.1 μm) from comparator/peak hold processor 25*c* (S18).

Distance/substance detection processor 27*a* temporarily stores the output (information of the peak of the intensity value of reflection light RV1) of reflection light RV1 of reference light LS1 having the first wavelength from comparator/peak hold processor 25*c* in memory 27*b* (S19).

Meanwhile, in a case where information of the even-numbered pixel (even-numbered target area PT) in any one line of detection area K in the horizontal direction is acquired in step S16 (S17, N), distance/substance detection processor 27*a* temporarily stores the output (information of the peak of the intensity value of reflection light RV2) of reflection light RV2 of measuring light LS2 having the second wavelength (for example, 1.45 μm) from comparator/peak hold processor 25*c* in memory 27*b* (S20).

Distance/substance detection processor 27*a* performs the interpolation process described with reference to FIGS. 8 and 9 based on the information of the peak of the intensity value of reflection light RV1 in the odd-numbered target area and the information of the peak of the intensity value of reflection light RV2 in the even-numbered target area which are stored in memory 27*b* (S21).

Distance/substance detection processor 27*a* determines whether or not the specific substance is detected in detection area K based on the interpolation process result of step S21, the information items of the peaks of the intensity values of reflection light beams RV1 and RV2 which are temporarily stored in memory 27*b* in steps S19 and S20, and the predetermined detection threshold (for example, detection threshold M) (S22). Detection result filter 27*c* filters the information related to the specific substance of the distance from invisible light sensor NVSS within the detection area is within the predetermined detecting target distance or the detecting target distance range designated from controller 11 based on the output of distance/substance detection processor 27*a* and the information of the detecting target distance or detecting target distance range, and extracts the filtered information.

Display processor 29 generates the substance position image data (display data) indicating the position of the specific substance in detection area K for each distance from invisible light sensor NVSS by using the output of detection result filter 27*c*, as an example of the information related to the specific substance of which the distance from invisible light sensor NVSS within the detection area is within the detecting target distance or the detecting target distance range (S23). The respective operations of step S11 to step S23 are performed for every line within the detection area of one frame (projection cycle).

After step S23, in a case where the execution of the respective operations of steps S11 to step S23 on all target areas PT within the detection area is not ended (S24, N), the respective operations of steps S11 to step S23 are repeated until the execution of the respective operations of step S11 to step S23 on all target areas PT within detection area K is ended.

Meanwhile, in a case where the execution of the respective operations of step S11 to step S23 on all target areas PT within detection area K is ended (S24, Y), and in a case where the application of reference light LS1 and measuring light LS2 is continued (S25, Y), the operation of invisible light sensor NVSS is returned to step S11. In a case where the application of reference light LS1 and measuring light LS2 is not continued (S25, N), the operation of invisible light sensor NVSS is ended.

As stated above, invisible light sensor NVSS according to the present exemplary embodiment irradiates detection area K having a plurality of target areas PT with reference light LS1 having the first wavelength from first projection light source 13 through the surface irradiation using optical scanning, irradiates the detection area with measuring light LS2 having the second wavelength different from the first wavelength from second projection light source 15, and detects the specific substance in detection area K based on reflection light RV1 of reference light LS1 from first projection light source 13 and reflection light RV2 of measuring light LS2 from second projection light source 15.

Accordingly, since invisible light sensor NVSS applies reference light LS1 and measuring light LS2 having different wavelengths from different light sources (first projection light source 13 and second projection light source 15) by performing the surface irradiation using the optical scanning on predetermined detection area K once, it is possible to further reduce a time difference between the projection timings of reference light LS1 and measuring light LS2 from the respective light sources (first projection light source 13 and second projection light source 15) than that in a case where the entire detection area K is irradiated with only measuring light LS2 after the entire detection area K is irradiated with only reference light LS1. Since invisible light sensor NVSS is able to reduce a time difference between the projection timing of reference light LS1 and the projection timing of measuring light LS2, it is possible to decrease change between a status of detection area K at the projection timing of reference light LS1 and a status of detection area K at the projection timing of measuring light LS2, and it is possible to suppress the erroneous detection of the measuring target substance (specific substance) in detection area K.

Second Exemplary Embodiment

Figure 23:
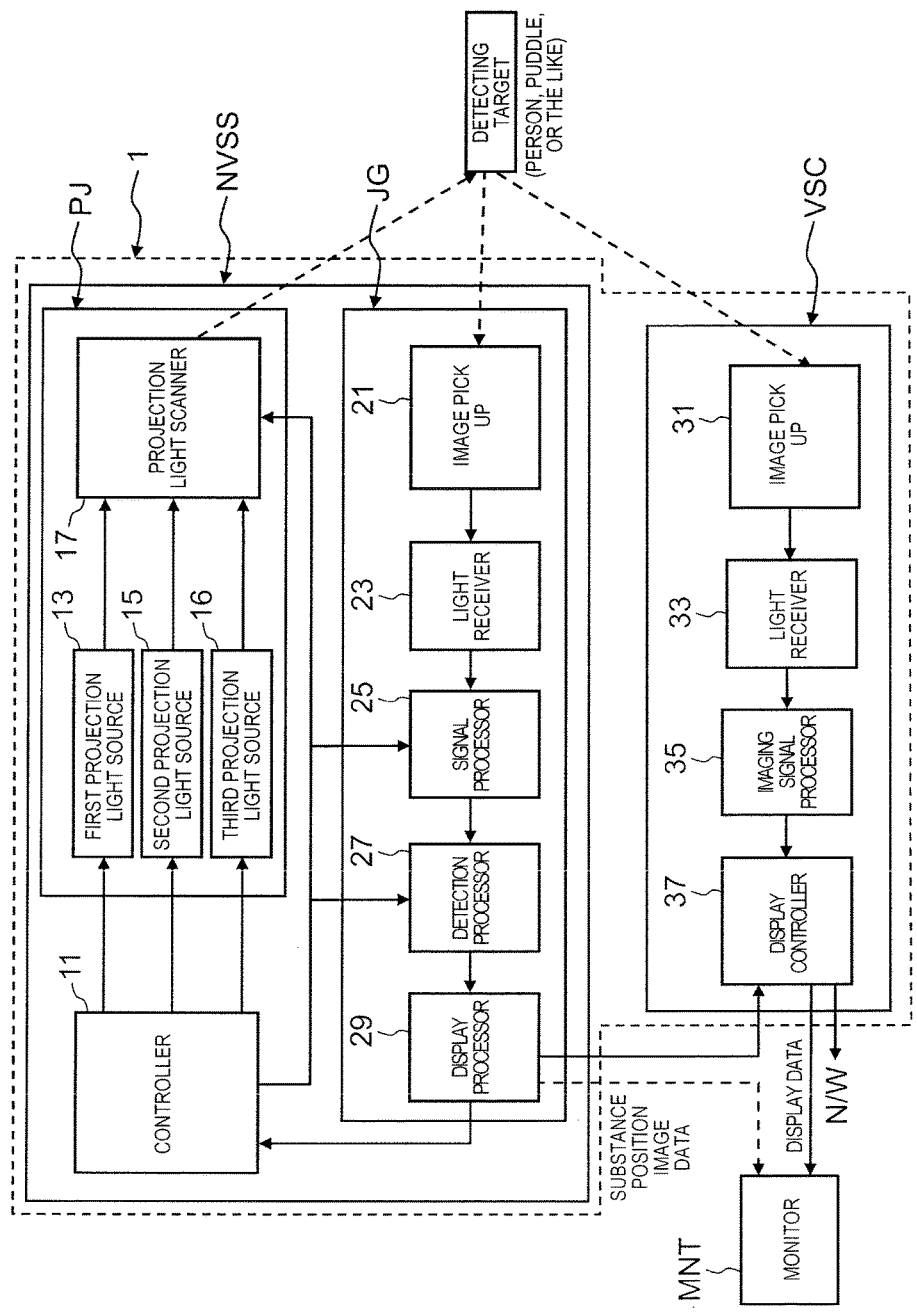
FIG. 23 is a block diagram showing a first example of an internal configuration of a detection camera including an invisible light sensor according to a second exemplary embodiment in detail.
Figure 24:
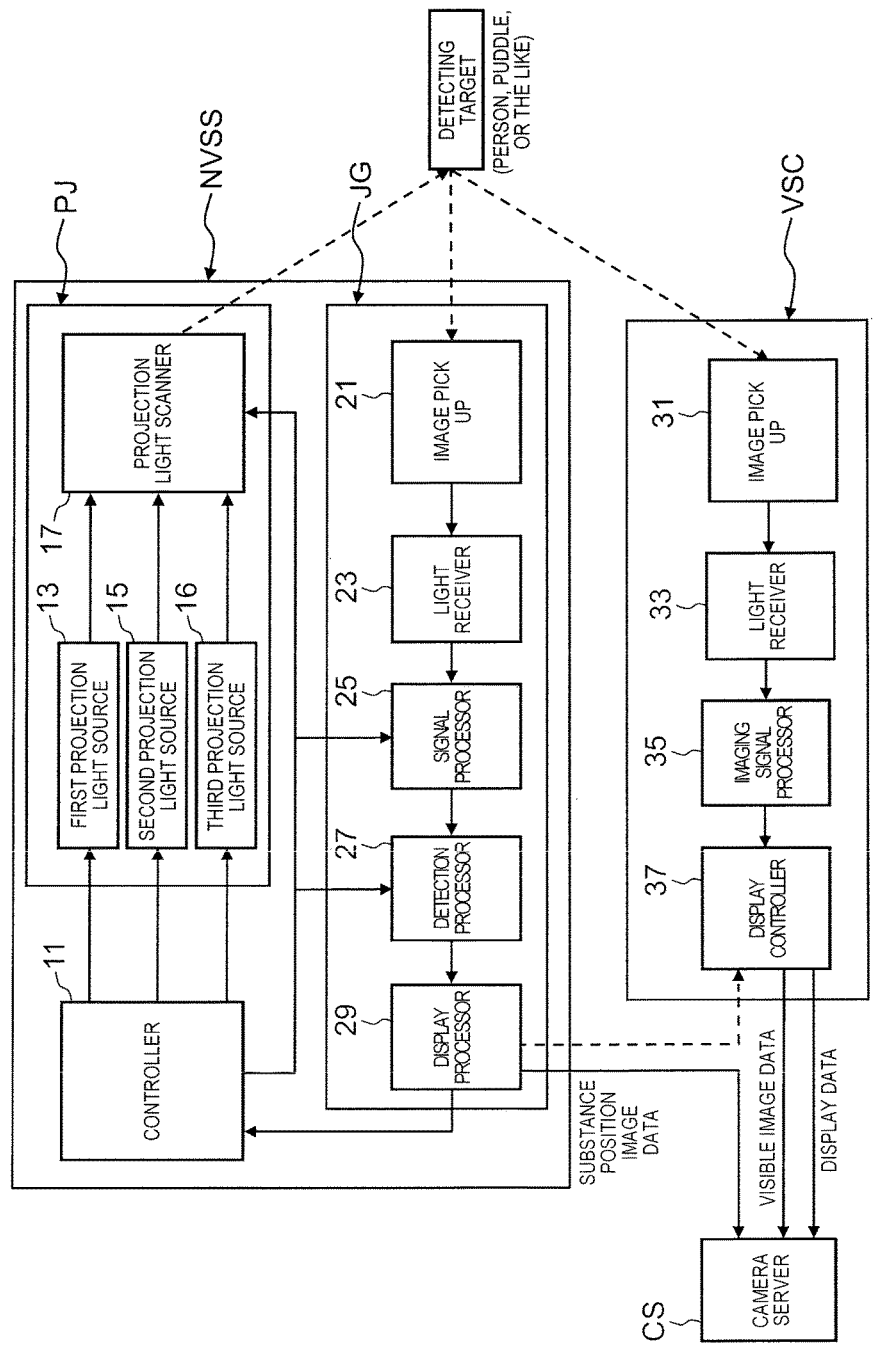
FIG. 24 is a block diagram showing a second example of the internal configuration of the detection camera including the invisible light sensor according to the second exemplary embodiment in detail.

In a second exemplary embodiment, an example of invisible light sensor NVSS that determines whether or not the specific substance of detection area K is detected by using three kinds of light beams (reference light LS1, and measuring light beams LS2 and LS3) will be described (see FIGS. 23 and 24). FIG. 23 is a block diagram showing a first example of an internal configuration of detection camera 1 including invisible light sensor NVSS according to the second exemplary embodiment in detail. FIG. 24 is a block diagram showing a second example of the internal configuration of detection camera 1 including invisible light sensor NVSS according to the second exemplary embodiment in detail. In the description of FIGS. 23 and 24, the contents different from the detailed internal configuration of detection camera 1 including invisible light sensor NVSS shown in FIG. 3 will be described. The same contents will be assigned the same reference numeral, and the description thereof will be omitted.

In invisible light sensor NVSS shown in FIGS. 23 and 24, first projection light source 13, second projection light source 15, and third projection light source 16 are provided in light projector PJ.

Third projection light source 16 as an example of a third light source projects measuring light LS3 (for example, infrared light) which is invisible light having a third wavelength (for example, 2.8 μm) different from the above-described first wavelength and second wavelength onto the target area of detection area K via projection light scanner 17 through the surface irradiation using the optical scanning, in response to the input of timing signal TR for light scanning from timing controller 11a. In the present exemplary embodiment, measuring light LS3 projected from third projection light source 16 is used for determining whether or not the specific substance is detected in detection area K of invisible light sensor NVSS. The third wavelength of measuring light LS3 which is 2.8 μm is a wavelength appropriate in a case where the specific substance as the measuring target substance is gas such as carbon dioxide.

In FIG. 23, display controller 37 may display the display data generated through the combination process on monitor MNT, or may transmit the display data to another external connection device (not shown) via an external network (N/W).

(Projection Patterns of Reference Light and Measuring Light in Invisible Light Sensor)

Hereinafter, the projection patterns of reference light LS1 and measuring light beams LS2 and LS3 in invisible light sensor NVSS according to the present exemplary embodiment will be described with reference to FIGS. 25A, 25B, 25C, and 26.

Figures 25A, 25B, 25C:
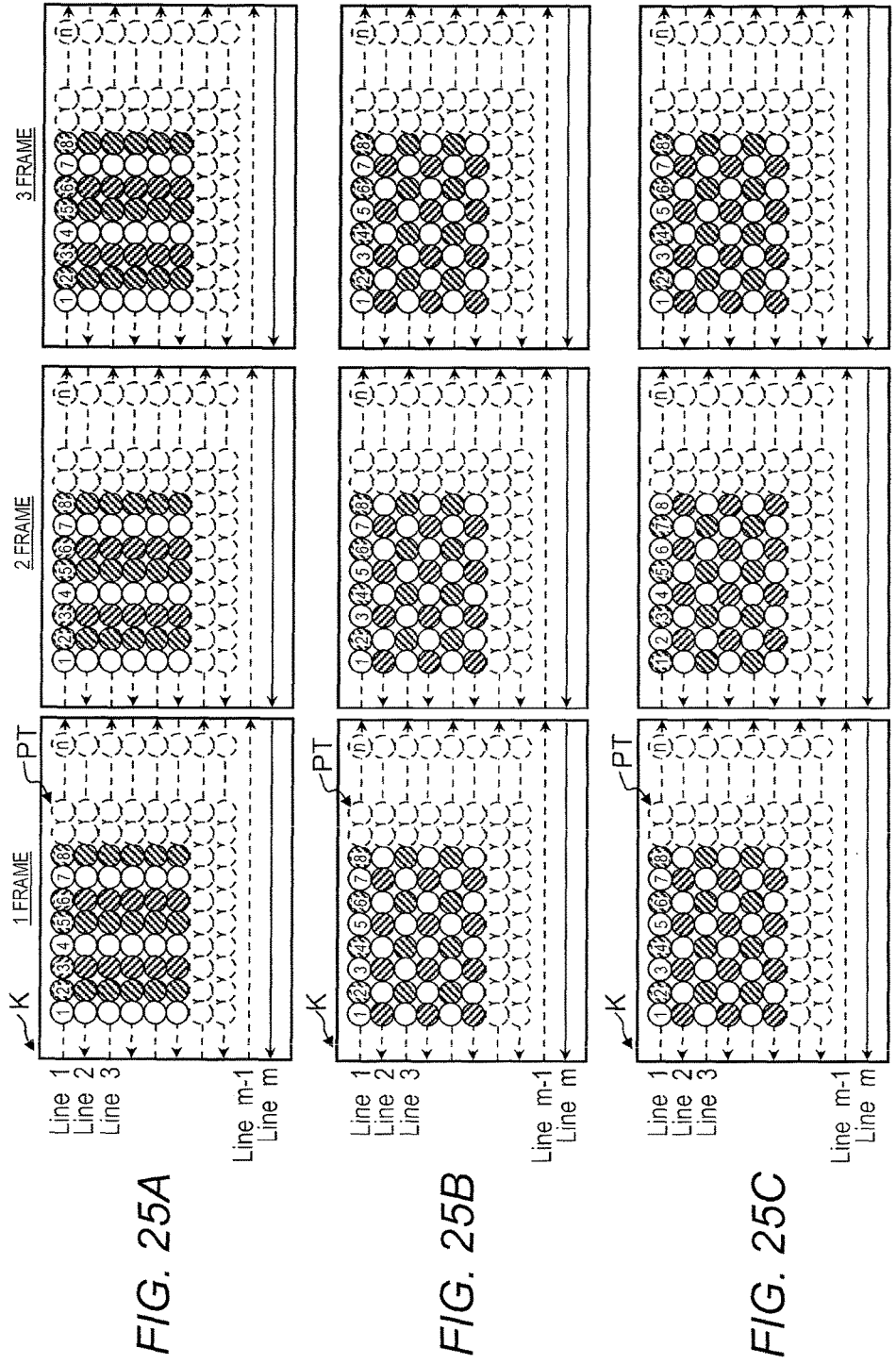
FIG. 25A is an explanatory diagram showing an example of a tenth projection pattern formed by a first projection light source and a second projection light source according to the second exemplary embodiment.
FIG. 25B is an explanatory diagram showing an example of an eleventh projection pattern formed by the first projection light source and the second projection light source according to the second exemplary embodiment.
FIG. 25C is an explanatory diagram showing an example of a twelfth projection pattern formed by the first projection light source and the second projection light source according to the second exemplary embodiment.
Figure 26:
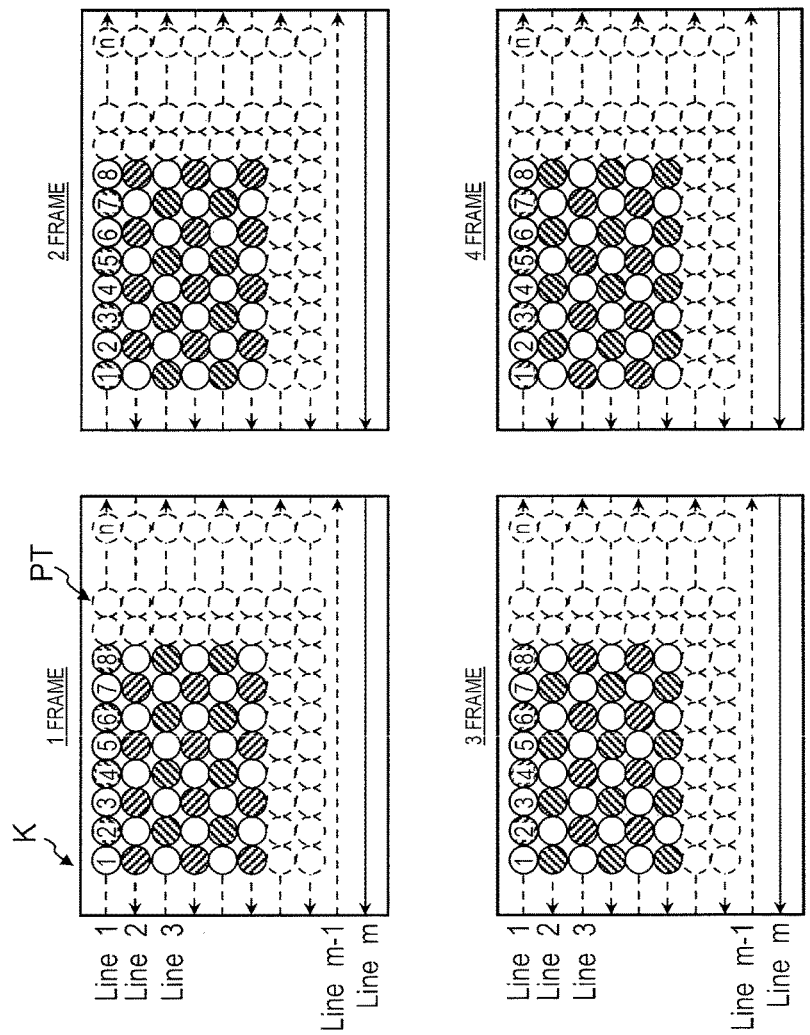
FIG. 26 is an explanatory diagram showing an example of a thirteenth projection pattern formed by the first projection light source and the second projection light source according to the second exemplary embodiment.

FIG. 25A is an explanatory diagram showing an example of a tenth projection pattern formed by first projection light source 13 and second projection light source 15 according to the second exemplary embodiment. FIG. 25B is an explanatory diagram showing an example of an eleventh projection pattern formed by first projection light source 13 and second projection light source 15 according to the second exemplary embodiment. FIG. 25C is an explanatory diagram showing an example of a twelfth projection pattern formed by first projection light source 13 and second projection light source 15 according to the second exemplary embodiment; FIG. 26 is an explanatory diagram showing an example of a thirteenth projection pattern formed by first projection light source 13 and second projection light source 15 according to the second exemplary embodiment.

In the tenth projection pattern according to the present exemplary embodiment shown in FIG. 25A, invisible light sensor NVSS alternately switches between reference light LS1, measuring light LS2, and measuring light LS3 to irradiate each target area PT adjacent in the horizontal direction of the initial line (Line 1) of detection area K and also alternately switches between reference light LS1, measuring light LS2, and measuring light LS3 to irradiate each target area PT adjacent in the horizontal direction in the next line (Line 2) in the same manner, for every frame. Accordingly, since invisible light sensor NVSS switches between reference light LS1, measuring light LS2, and measuring light LS3 such that these light beams are adjacent to irradiate each target area PT adjacent in the horizontal direction which correspond to the pixels constituting the visible light image data of detection area K, it is possible to decrease a time difference between the projection timing of reference light LS1, the projection timing of measuring light LS2, and the projection timing of measuring light LS3, and it is possible to detect whether or not the specific substance is present in the target areas of detection area K in the horizontal direction with high accuracy based on reflection light beams RV1, RV2, and RV3 of reference light LS1, measuring light LS2, and measuring light LS3 for adjacent pixels in the horizontal direction.

Unlike the tenth projection pattern, in the eleventh projection pattern according to the present exemplary embodiment shown in FIG. 25B, invisible light sensor NVSS alternately irradiates each target area PT adjacent in the horizontal direction of the odd-numbered line of detection area K with reference light LS1 and measuring light LS2, and alternately irradiates each target area PT adjacent in the horizontal direction of the even-numbered line of detection area K with measuring light LS3 and reference light LS1. Accordingly, since invisible light sensor NVSS is able to irradiate surrounding target areas PT adjacent to target area PT which is irradiated with measuring light LS2 or measuring light LS3 with reference light LS1, it is possible to perform the interpolation process on the intensity value of reflection light RV0 in a case where it is assumed that target area PT irradiated with measuring light LS2 or measuring light LS3 (in other words, is not irradiated with reference light LS1) is irradiated with reference light LS1 with high accuracy, and it is possible to suppress the erroneous detection of the specific substance by performing the detection process of the specific substance using the output after the interpolation process.

Unlike the eleventh projection pattern, in the twelfth projection pattern according to the present exemplary embodiment shown in FIG. 25C, since invisible light sensor NVSS switches the application order of reference light LS1 and measuring light LS2 to the line of detection area K in the horizontal direction and the application order of measuring light LS3 and reference light LS1 to the line of detection area K in the horizontal direction for each frame indicating the surface irradiation of the entire detection area K, reflection light beams RV1 and RV2 of reference light LS1 and measuring light LS2 and reflection light beams RV3 and RV1 of measuring light LS3 and reference light LS1 to target areas PT of detection area K are compared between the frames, and thus, reflection light beams RV1 and RV2 of reference light LS1 and measuring light LS2 and reflection light beams RV3 and RV1 of measuring light LS3 and reference light LS1 in the same target area PT are acquired. Thus, it is possible to detect the specific substance in the line of the detection area K in the horizontal direction with higher accuracy than that in a case where reference light LS1 and measuring light LS2, and measuring light LS3 and reference light LS1 are not projected on the same target area PT, and it is possible to improve display resolution of the detection result of the specific substance.

In the thirteenth projection pattern according to the present exemplary embodiment shown in FIG. 26, since invisible light sensor NVSS switches the application order of measuring light LS2 and measuring light LS3 for every two frames on a per two-frame basis and respectively switches the application order of reference light LS1 and measuring light LS2 and the application order of measuring light LS3 and reference light LS1 in the first-half frame and the second-half frame of two frames, it is possible to irradiate target area PT of detection area K with reference light LS1, measuring light LS2, and measuring light LS3, and it is possible to-detect the specific substance in target areas PT of detection area K in the horizontal direction and the vertical direction with high accuracy. Thus, it is possible to improve display resolution of the detection result of the specific substance.

As mentioned above, invisible light sensor NVSS according to the present exemplary embodiment applies measuring light LS3 having the third wavelength different from the first wavelength and the second wavelength from third projection light source 16 through the surface irradiation using the optical scanning, and detects the specific substance in detection area K based on reflection light RV1 of reference light LS1 from first projection light source 13, reflection light RV2 of measuring light LS2 from second projection light source 15, and reflection light RV3 of measuring light LS3 from third projection light source 16.

Accordingly, since invisible light sensor NVSS applies reference light LS1, measuring light LS2, and measuring light LS3 having different wavelengths from different light sources (first projection light source 13, second projection light source 15, and third projection light source 16) by performing the surface irradiation using the optical scanning on predetermined detection area K once, it is possible to further reduce a time difference between the projection timings of reference light LS1, measuring light LS2, and measuring LS3 from the respective light sources (first projection light source 13, second projection light source 15, and third projection light source 16) than that in a case where the entire detection area K is irradiated with only measuring light LS3 after the entire detection area K is irradiated with only reference light LS1 and then the entire detection area K is irradiated with only measuring light LS2. Since invisible light sensor NVSS can decrease the time difference between the projection timing of reference light LS1 and the projection timings of measuring light LS2 and measuring light LS3, it is possible to decrease a change between a status of detection area K at the projection timing of reference light LS1 and a status of detection area K at the projection timing of measuring light LS2 or measuring light LS3, and it is possible to suppress the erroneous detection of the measuring target substance (specific substance) in detection area K. Since invisible light sensor NVSS irradiates detection area K not only with measuring light LS2 but also with measuring light LS3, it is possible to increase the kind of the specific substance capable of being detected by invisible light sensor NVSS.

As the above-described detecting target distance range, not one range but a plurality of ranges may be set. For example, the detecting target distance range includes a first range of 2 to 3 m, and a second range of 6 to 8 m. Similarly, as the above-described detecting target distance, not one value but a plurality of values may be set. In a case where the plurality of detecting target distances is input, controller 11 may calculate the detecting target distance range depending on each detecting target distance, and may set the calculated detecting target distance range. The plurality of detecting target distances or detecting target distance ranges is able to be set in this manner, and thus, it is possible to set the detection condition of invisible light sensor NVSS depending on the installation environment of invisible light sensor NVSS.

The number of set detecting target distances or detecting target distance ranges may be arbitrarily increased or decreased. Accordingly, it is possible to set the detection condition of invisible light sensor NVSS depending on the complexity of the installation environment of invisible light sensor NVSS. For example, the number of detecting target distances or detecting target distance ranges is set to be a large value in a case where the environment is complicated (for example, a case where there is a plurality of shelves in detection area K), and the number of detecting target distances or detecting target distance ranges is set to be a small value in a case where the environment is simple (for example, a case where there is no shelf in detection area K).

The plurality of detecting target distances or detecting target distance ranges may be previously set, or may be arbitrarily set by the user using camera server CS or communication terminal MT. Alternatively, an input capable of setting these distances and ranges may be provided in invisible light sensor NVSS. As in the above-described specific examples, it is necessary to set any one of an upper limit and a lower limit to the detecting target distance range without setting any one thereof. For example, the detecting target distance range such as 100 m or more, or 5 m or less may be set.

In the respective above-described exemplary embodiments, light projector PJ, image judge JG, and visible light camera VSC may be separately provided. For example, light projector PJ and image judge JG may be held by different housings. Similarly, light projector PJ and visible light camera VSC may be held by different housings. First projection light source 13, second projection light source 15, and third projection light source 16 may be separately provided.

Image judge JG and visible light camera VSC are preferably provided in the same housing. More specifically, image pick up 21 used for forming the substance position image data and image pick up 31 used for forming the visible light image data are preferably provided in the same housing. Image pick up 21 and image pick up 31 are provided in the same housing, and thus, the light receiving positions of two light receivers thereof can come into contact with each other. That is, the detection positions of the substance position image data and the visible light image data can come into contact with each other. Accordingly, a difference between the substance position image data and the visible light image data can be reduced, and a load of the process of combining the visible light image data with the substance position image data by means of display controller 37 can be reduced.

The received signal may be processed by the external device (for example, camera server CS or communication terminal MT) of detection camera 1. The signal processing is equivalent to the processes of signal processor 25, detection processor 27, display processor 29, imaging signal processor 35, display controller 37, and controller 11 which are described above. The external device of detection camera 1 has the function related to the signal processing, and thus, the size of detection camera 1 can be reduced.

Although various exemplary embodiments will be described with reference to the drawings, it is needless to say that the present disclosure is not limited to the relevant examples. It is apparent that various change examples or modification examples can be derived without departing from the category described in claims by those skilled in the art, and it is understood that these examples are included in the technical scope of the present disclosure.

INDUSTRIAL APPLICABILITY

The present disclosure is useful as a substance detection sensor, a substance detection method, and a substance detection system which reduce a time difference between projection timings of measuring light and reference light onto a predetermined detection area and suppress erroneous detection of a measuring target substance in the detection area.

REFERENCE MARKS IN THE DRAWINGS 1 detection camera
11 controller
11a timing controller
13 first projection light source
15 second projection light source
16 third projection light source
17 projection light scanner
21, 31 image pick up
23, 33 light receiver
25 signal processor
25a I/V converter
25b amplifier
25c comparator/peak hold processor
27 detection processor
27a distance/substance detection processor
27b memory
27c detection result filter
29 display processor
35 imaging signal processor
37 display controller
FCLS condenser lens
CS camera server
HM person
JG image judge
K detection area
LS1 reference light
LS2, LS3 measuring light
MNT monitor
MT communication terminal
NVSS invisible light sensor
PJ light projector
PT, D1, D2, D3, D4, D5 target area
TR timing signal for light scanning
RF light output signal
RLM1, RLM2 reflection mirror
RV0 reflection light
RV1 reference reflection light
RV2, RV3 measuring reflection light
SBT circuit board
SCM scanning mirror
VSC visible light camera
WT, WT1, WT2, WT3 puddle

The invention claimed is:

1. A substance detection sensor comprising:
   a first light source that irradiates a detection area including a plurality of target areas with reference light having a first wavelength through surface irradiation using optical scanning;
   a second light source that irradiates the detection area with first measuring light having a second wavelength different from the first wavelength through the surface irradiation using the optical scanning; and
   a substance detector that detects a specific substance in the detection area based on reflection light of the reference light from the first light source and reflection light of the first measuring light from the second light source.

2. The substance detection sensor of claim 1, further comprising:
   an irradiation controller that controls irradiation timings when the detection area is irradiated with the reference light from the first light source and the first measuring light from the second light source for every target area corresponding to a single pixel in a time-division manner,
   wherein the irradiation controller irradiates every adjacent target area in a horizontal direction of the detection area with the reference light and the first measuring light from the first light source and the second light source while alternately switching between the reference light and the first measuring light.

3. The substance detection sensor of claim 2,
   wherein the irradiation controller irradiates every adjacent target area in a vertical direction of the detection area with the reference light and the first measuring light from the first light source and the second light source while alternately switching between the reference light and the first measuring light.

4. The substance detection sensor of claim 3,
   wherein the irradiation controller switches an irradiation order of the detection area with the reference light from the first light source and the first measuring light from the second light source for every frame indicating the surface irradiation performed on the entire detection area.

5. The substance detection sensor of claim 2,
   wherein the irradiation controller irradiates every adjacent target area in a vertical direction of the detection area with the reference light and the first measuring light from the first light source and the second light source while alternately switching between the reference light and the first measuring light.

6. The substance detection sensor of claim 5,
   wherein the irradiation controller switches an irradiation order of the detection area with the reference light from the first light source and the first measuring light from the second light source for each frame indicating the surface irradiation performed on the entire detection area.

7. The substance detection sensor of claim 1, further comprising:
   an irradiation controller that controls irradiation timings when the detection area is irradiated with the reference light from the first light source and the first measuring light from the second light source for every target area corresponding to a single pixel in a time-division manner, wherein the irradiation controller irradiates every adjacent target area in a horizontal direction of the detection area with the reference light or the first measuring light from the first light source or the second light source, and irradiates every adjacent target area in a vertical direction of the detection area with the reference light and the first measuring light from the first light source and the second light source while alternately switching between the reference light and the first measuring light.

8. The substance detection sensor of claim 5, wherein the irradiation controller switches an irradiation order of the detection area with the reference light from the first light source and the first measuring light from the second light source for every frame indicating the surface irradiation performed on the entire detection area.

9. The substance detection sensor of claim 1, further comprising:

an irradiation controller that controls irradiation timings when the detection area is irradiated with the reference light from the first light source and the first measuring light from the second light source for every target area corresponding to a single pixel in a time-division manner, wherein the irradiation controller irradiates the same target area with the reference light and the first measuring light at different timings.

10. The substance detection sensor of claim 1, further comprising:

a third light source that irradiates the detection area with second measuring light having a third wavelength different from the first wavelength and the second wavelength through the surface irradiation using the optical scanning, wherein the substance detector detects a specific substance in the detection area based on reflection light of the reference light from the first light source, reflection light of the first measuring light from the second light source, and reflection light of the second measuring light from the third light source.

11. The substance detection sensor of claim 10, further comprising:

an irradiation controller that controls irradiation timings when the detection area is irradiated with the reference light from the first light source, the first measuring light from the second light source, and the second measuring light from the third light source for every target area corresponding to a single pixel in a time-division manner, wherein the irradiation controller irradiates every adjacent target area in a horizontal direction of the detection area with the reference light, the first measuring light, and the second measuring light from the first light source, the second light source, and the third light source while switching between the reference light, the first measuring light, and the second measuring light.

12. The substance detection sensor of claim 10, further comprising:

an irradiation controller that controls irradiation timings when the detection area is irradiated with the reference light from the first light source, the first measuring light from the second light source, and the second measuring light from the third light source for every target area corresponding to a single pixel in a time-division manner, wherein the irradiation controller alternately irradiates every adjacent odd-numbered target area in a horizontal direction with the reference light and the first measuring light from the first light source and the second light source, and alternately irradiates every adjacent even-numbered target area in the horizontal direction with the second measuring light and the reference light from the third light source and the first light source.

13. The substance detection sensor of claim 12, wherein the irradiation controller switches an irradiation order of the detection area with the reference light and the first measuring light in the horizontal direction and an irradiation order of the detection area with the second measuring light and the reference light in the horizontal direction for every frame indicating the surface irradiation performed on the entire detection area.

14. The substance detection sensor of claim 12, wherein the irradiation controller uses frames twice as many as the frame indicating the surface irradiation performed on the entire detection area, as a unit, switches an irradiation order of the detection area with the first measuring light and the second measuring light for every two frames, and switches the irradiation order of the detection area with the reference light and the first measuring light and the irradiation order of the detection area with the second measuring light and the reference light in the first frame and the second frame of the two frames.

15. The substance detection sensor of claim 2, wherein the substance detector performs an interpolation process on intensity of the reflection light of the reference light or the first measuring light in a specific target area of the detection area which is not irradiated with the reference light or the first measuring light by using an average value of intensity values of the reflection light of the reference light or the first measuring light for the plurality of target areas adjacent to the specific target area.

16. The substance detection sensor of claim 15, wherein, in a case where four target areas around the specific target area are irradiated with the reference light or the first measuring light, the substance detector performs the interpolation process on the intensity of the reflection light of the reference light or the first measuring light in the specific target area by using an average value of intensity values of the reflection light of the reference light or the first measuring light in two target areas corresponding to a smaller difference of a difference between intensity values of the reflection light of the reference light or the first measuring light in two adjacent target areas in a vertical direction of the specific target area and a difference between intensity values of the reflection light of the reference light or the first measuring light in the two adjacent target areas in a horizontal direction of the specific target area.

17. The substance detection sensor of claim 1, further comprising:

an imager that images the detection area, wherein the imager combines image data of the detection area imaged by the imager with information regarding the specific substance detected by the substance detector, and displays the combined resultant on a display.

18. A substance detection method of a substance detection sensor, comprising:
- a step of irradiating a detection area including a plurality of target areas with reference light having a first wavelength from a first light source through surface irradiation using optical scanning;
- a step of irradiating the detection area with first measuring light having a second wavelength different from the first wavelength from a second light source through the surface irradiation using the optical scanning; and
- a step of detecting a specific substance in the detection area based on reflection light of the reference light from the first light source and reflection light of the first measuring light from the second light source.

19. A substance detection system in which a substance detection sensor and an external connection device are connected,
wherein the substance detection sensor includes
- a first light source that irradiates a detection area including a plurality of target areas with reference light having a first wavelength through surface irradiation using optical scanning,
- a second light source that irradiates the detection area with first measuring light having a second wavelength different from the first wavelength through the surface irradiation using the optical scanning,
- a substance detector that detects a specific substance in the detection area based on reflection light of the reference light from the first light source and reflection light of the first measuring light from the second light source, and
- an output that outputs information regarding the specific substance detected by the substance detector to the external connection device.

* * * * *